us010265357B2

(12) United States Patent
Laer et al.

(10) Patent No.: US 10,265,357 B2
(45) Date of Patent: Apr. 23, 2019

(54) COMPOSITIONS, METHODS AND USES FOR TREATING SOLID TUMORS USING LCMV-GP-VSV PSEUDOTYPE VECTORS

(71) Applicant: ViraTherapeutics GmbH, Innsbruck (AT)

(72) Inventors: Dorothee Von Laer, Innsbruck (AT); Tsanan Heimann, Mainz (DE)

(73) Assignee: VIRATHERAPEUTICS GMBH, Innsbruck (AT)

(*) Notice: Subject to any disclaimer, the term of this patent is extended or adjusted under 35 U.S.C. 154(b) by 118 days.

(21) Appl. No.: 14/306,065

(22) Filed: Jun. 16, 2014

(65) Prior Publication Data
US 2014/0301992 A1 Oct. 9, 2014

Related U.S. Application Data

(63) Continuation-in-part of application No. 13/123,175, filed as application No. PCT/EP2009/007230 on Oct. 8, 2009.

(30) Foreign Application Priority Data

Oct. 8, 2008 (DE) .................. 10 2008 050 860

(51) Int. Cl.
A61K 35/766 (2015.01)
C12N 9/12 (2006.01)

(52) U.S. Cl.
CPC .......... A61K 35/766 (2013.01); C12N 9/1211 (2013.01); C12Y 207/01021 (2013.01); C12N 2760/20232 (2013.01); C12N 2760/20243 (2013.01); C12N 2810/6072 (2013.01)

(58) Field of Classification Search
CPC ............. C12N 15/86; C12N 9/1211; C12N 2760/20232; C12N 2760/20243; C12N 2810/6072; C12Y 207/01021; A61K 35/766
See application file for complete search history.

(56) References Cited

U.S. PATENT DOCUMENTS

2007/0059291 A1* 3/2007 McCray, Jr. ......... C07K 14/005
424/93.2
2011/0250188 A1 10/2011 Von Laer et al.

FOREIGN PATENT DOCUMENTS

EP 1006196 B1 11/1999
WO 2003005964 A2 1/2003
WO 2006008074 A1 1/2006

OTHER PUBLICATIONS

Bergman et al 2007, Int. J. Cancer. 121:425-430.*
Miletic et al 2004, Hum. Gene Therapy 15:1091-1100.*
Pereboeva et al 2003, Stem Cells 21:389-404.*
Beyer et al 2002, J. Virol 76:1488-1495.*
Fernandez et al, J. Virol. 76(2):895-904, 2002.*
Garbutt et al, J. Virol. 78(10): 5458-5465, 2004.*
Bruns et al, Virology 137:49-57, 1984.*
Power et al, Mol. Ther. 15(1):123-130, 2007.*
Guo et al, Biochim. Biophys. Acta 1785:217-231, 2008; available online Feb. 15, 2008.*
Beyer et al., "Recombinant Expression of Lymphocytic Chroriomeningitis Virus Strain WE Glycoproteins: a Single Amino Acid Makes the Difference" XP-002347069; Journal of Virology, Jan. 2001; vol. 75, No. 2, p. 1061-1064.
European Search Report for Application No. 13153949.6-1410; dated Apr. 29, 2013; 6 pgs.
Muik, et al., "Pseudotyping Vesicular Stomatitis Virus with Lymphocytic Choriomenengitis Virus Glycoproteins Enhances Infectivity for Glioma Cells and Minimizes Neurotropism" Journal of Virology, Jun. 2011, vol. 85, No. 11, XP-002695439; p. 5679-5684.
Johnson et al., "Specific Targeting to CD4 Cells of Recombinant Vesicular Stomatitis Viruses Encoding Human Immunodeficiency Virus Envelope Proteins," Journal of Virology, Jul. 1997, p. 5060-5068, vol. 71, No. 7, 10 pages.
Majid et al., "Evaluating Replication-Defective Vesicular Stomatitis Virus as a Vaccine Vehicle," Journal of Virology, Jul. 2006, p. 6993-7008, vol. 80, No. 14, 17 pages.
Ogino et al., "Use of Vesicular Stomatitis Virus Pseudotypes Bearing Hantaan or Seoul Virus Envelope Proteins in a Rapid and Safe Neutralization Test," Journals.asm.org, Clinical and Diagnostic Laboratory Immunology, Jan. 2003, p. 154-160, vol. 10, No. 1, Received Apr. 5, 2002, 8 pages.
Bruns et al., 1984, Virology 137:49-57.
Schnell et al 1996, Proc. Natl. Acad. Sci. (USA) 93:11359-11365.
Lichty et al 2004, Trends in Mol. Med. 10:210-216.
Lee et al, 2006, Vaccine 24:2928-2934.
Ahmed et al., "Immune Response in the Absence of Neurovirulence in Mice Infected with M Protein Mutant Vesicular Stomatitis Virus", Journal of Virology: 82(18): pp. 9273-9277 (Sep. 2008).
Barber, "Vesicular Stomatitis Virus as an Oncolytic Vector", Viral Immunol, 17(4): pp. 516-527 (2004).
Beyer et al., "Oncoretrovirus and Lentivirus Vectors Pseudotyped with Lymphocytic Choriomeningitis Virus Glycoprotein: Generation, Concentration, and Broad Host Range", Journal of Virology, 76(3): pp. 516-527 (Feb. 2002).
Carlsson et al., "Liquid-Overlay Culture of Celular Spheroids", Recent Results Cancer Research, 95: pp. 1-23 (1984).
Culver et al., "In Vivo Gene Transfer with Retroviral Vector-Producer Cells for Treatment of Experimental Brain Tumors", Science, 256(5063): pp. 1550-1552 (Jun. 12, 1992).
Cutter et al., "Gene Therapeutics: the Future of Brain Tumor Therapy?", Expert Review of Anticancer Therapy, 6 (7): pp. 1053-1 034 (2006).
Dai et al., "Glioma Models", Biochim Biophys Acta., 1551(1): pp. M19-M27 (Aug. 31, 2001).
Desforges et al., "Different Host-Cell Shutoff Strategies Related to the Matrix Protein Lead to Persistence of Vesicular Stomatitis Virus Mutants on Fibroblast Cells", Virus Res., 76(1): pp. 87-102 (Jul. 2001).

(Continued)

Primary Examiner — Kevin K Hill
(74) Attorney, Agent, or Firm — Polsinelli PC

(57) ABSTRACT

Embodiments of the present invention relate to compositions and methods for producing recombinant VSV viruses. In accordance with these embodiments, viral vectors can include a glycoprotein GP of the lymphocyte choriomeningitis virus (LCMV) instead of the G protein of the VSV. Other embodiments relate to cells for producing a LCMV-GP-pseudotyped VSV vectors. Embodiments also relate to the use of the vectors and cells as part of a pharmaceutical composition for the treatment of solid tumors.

23 Claims, 11 Drawing Sheets

(56) References Cited

OTHER PUBLICATIONS

Finke et al., "Recombinant Rhabdoviruses: Vectors for Vaccine Development and Gene Therapy", Curr Top Microbiol Immunol, 292: pp. 165-200 (2005).
Fischer et al.. "A Retroviral Packaging Cell Line for Pseudotype Vectors Based on Glioma-Infiltrating Progenitor Cells", Journal of Gene Medicine, 9: pp. 335-344 (2007).
Fukuhara et al., "Oncolytic Herpes Simplex Virus Vector G47? in Combination with Androgen Ablation for the Treatment of Human Prostate Adenocarcinoma", Clin Cancer Res., 11(21): pp. 7886-7890 (Nov. 1, 2005).
Garbutt et al., "Properties of Replication-Competent Vesicular Stomatitis Virus Vectors Expressing Glycoproteins of Filoviruses and Arenaviruses," J Virol., 78(10): pp. 5458-5465 (May 2004).
Ge et al., "Generating Vesicular Stomatitis Virus Pseudotype Bearing the Severe Acute Respiratory Syndrome Coronavirus Spike Envelope Glycoprotein for Rapid and Safe Neutralization Test or Cell-Entry Assay", Ann N Y Acad Sci., 1081: pp. 246-248 (2006).
Haller et al., "The Interferon Response Circuit: Induction and Suppression by Pathogenic Viruses", Virology, 344 (1): pp. 119-130, (Jan. 5, 2006).
Hanika et al., "Use of Influenza C Virus Glycoprotein HEF for Generation of Vesicular Stomatitis Virus Pseudotypes", J Gen Virol., 86(Pt 5): pp. 1455-1465 (May 2005).
Holland et al., "Gliomagenesis: Genetic Alterations and Mouse Models", Nat Rev Genet., ;2(2): pp. 120-129 (Feb. 2001).
Irie et al., "Modifications of the PSAP Region of the Matrix Protein Lead to Attenuation of Vesicular Stomatitis Virus in Vitro and in Vivo", J Gen Viral., 88 (Pt 9): pp. 2559-2567 (Sep. 2007).
Janzen et al., "A Monomeric GTPase-Negative MxA Mutant with Antiviral Activity", J Virol, 74(17): pp. 8202-8206, (Sep. 2000).
Jayakar et al., "Identification of Two Additional Translation Products from the Matrix (M) Gene that Contribute to Vesicular Stomatitis Virus Cytopathology", J Virol., 76(16): pp. 8011-8018, (Aug. 2002).
Jiang et al, "Piuripotency of Mesenchymal Stem Cells Derived from Adult Marrow", Nature 418: pp. 41-49 (2000).
Kikuchi et al.. "Antitumor Activity of Interleukin 12 Against Interleukin 2-Transduced Mouse Glioma Cells" Cancer Lett.. 135: pp. 47-51 (1999).
Loew et al.. "Retroviral Vectors Containing Tel-Controlled Bidirectional Transcription Units for Simultaneous Regulation of Two Gene Activities", JMol GenMed, 2(1 ): pp. 107-118 (2006).
Lun et al., "Effects of Intravenously Administered Recombinant Vesicular Stomatitis Virus (VSV ? M51) on multifocal and Invasive Gliomas", J Natl Cancer Inst., 98(21 ): pp. 1546-1557 (Nov. 1, 2006).
Majewski et al., "Interleukin-12 Inhibits Angiogenesis Induced by Human Tumor Cells in Vivo", J. Invest. Dermatol., 106: pp. 1114-1118 (1996).
Miletic et al., "Retroviral Vectors Pseudotyped with Lymphocytic Choriomeningitis Virus", J. Virol., 73: pp. 6114-6116 (1999).
Miletic et al., "Selective Transduction of Malignant Glioma by Lentiviral Vectors Pseudotyped with Lymphocytic Choriomeningitis Virus Glycoproteins", Hum Gene Ther., 15: pp. 1091-1100 (Nov. 2004).
Miletic et al., "Normal Brain Cells Contribute to the Bystander Effect in Suicide Gene Therapy of Malignant Glioma", Clin Cancer Res, 13(22): pp. 6761-6768 (Nov. 15, 2007).
Miletic et al., "Bystander Killing of Malignant Glioma by Bone Marrow-Derived Tumor Infiltrating Progenitor Cells Expressing a Suicide Gene" Molecular Therapy 15(7): pp. 1373-1381 (Jul. 2007).
Owens et al., "Cytoplasmic Domain Requirement for Incorporation of a Foreign Envelope Protein into Vesicular Stomatitis Virus" J Virol. 67(1 ): pp. 360-365 (Jan. 1993).
Pavlovic et al., "Human and Mouse Mx Proteins Inhibit Different Steps of the Inftuenza Virus Multiplication Cycle" J Virol., 66(4): pp. 2564-2569 (Apr. 1992).
International Search Report for PCT/EP2009/007230, dated Mar. 4, 2010.

Written Opinion for PCT/EP2009/007230, dated Mar. 4, 2010.
Sakariassen et al., "Angiogenesis-Independent Tumor Growth Mediated by Stem-Like Cancer Cells" Proc Nail Acad Sci U S A, 103(44): pp. 16466-16471 (Oct. 31, 2006).
Shinosaki et al., "Prophylactic alpha interferon treatment increases the therapeutic index of oncolytic vesicular stomatitis virus virotherapy for edvanced hepatocellular carcinoma in immune-competent rats", J Virol., 79(21 ): pp. 13705-13713.
Shir et al., "Gene Therapy for Glioblastoma: Future Perspective for Delivery Systems and Molecular Targets", Cell Mol Neubiol, 21 (6): pp. 645-656, (Dec. 2001).
Short et al., Gene delivery to glioma cells in rat brain by grafting of a retrovirus packaging cell line. J Neurosci Res. 27(3): pp. 427-439 (Nov. 1990).
Spann et al., "Genetic Recombination During Coinfection of Two Mutants of Human Respiratory Syncytial Virus" J Virol., 77(20): pp. 11201-11211 (Oct. 2003).
Staeheli et al., "Inhibition of Vesicular Stomatitis Virus mRNA Synthesis by Human MxA Protein", J Viral. 65(8): pp. 4498-4501 (Aug. 1991).
Sumia et al., Inflammatory and Anti-glioma Effects of an Adenovirus Expressing Human Soluble Fms-like Tyrosine Kinase 3 Ligand (hsFll30: Treatment with hsFlt3L Inhibits Intracranial Glioma Progression. Molecular Therapy 10(6): pp. 1071-1084 (Dec. 2004).
Tani et al., "Replication-Competent Recombinant Vesicular Stomatitis Virus Encoding Hepatitis C Virus Envelope Proteins", J Virol., 81(16): pp. 8601-8612, (Aug. 2007) (Epub Jun. 6, 2007).
Toda et al., "In Situ Cancer Vaccination: An IL-12 Defective Vector/Replication-Competent Herpes Simplex Virus Combination Induces Local and Systemic Antitumor Activity", J. Immunol. 160: pp. 4457-4464 (1998).
Trajcevski et al., "Characterization of a semi-replicative gene delivery system allowing propagation of complementary defective retroviral vectors", J Gene Med., 7(3): pp. 276-287 (Mar. 2005).
Tyminski et al.. "Brain Tumor Oncolysis with Replication-Conditional Herpes Simplex Virus Type 1 Expressing the Prodrug-Activating Genes. CYP2B1 and Secreted Human Intestinal Carboxylesterase, in Combination with Cyclophosphamide and Irinotecan", Cancer Res., 65(15): pp. 6850-6857 (Aug. 1, 2005).
Wollman et al., "Variable Deficiencies in the Interferon Response Enhance Susceptibility to Vesicular Stomatitis Virus Oncolytic Actions in Glioblastoma Cells but not in Normal Human Glial Cells", J Virol., 81(3): pp. 1479-1491 (Feb. 2007).
Zimmer et al., "Cleavage at the Furin Consensus Sequence RAR/KR109 and Presence of the Intervening Peptide of the Respiratory Syncytial Virus Fusion Protein Are Dispensable for Virus Replication in Cell Culture," J Virol., 76(18): pp. 9218-9224, (Sep. 2002).
Brown. Kyle S. et al.; "Vesicular Stomatitis Virus-Based Vaccine Protects Hamsters Against Lethal Challenge with Andes Virus"; Journal of Virology; vol. 83. No. 23; p. 12781-12791; Dec. 2011.
Fukushi. Shuetsu, et al.; "Vesicular Stomatitis Virus Pseudotyped with Severe Acute Respiratory Syndrome Coronavirus Spike Protein"; Journal of General Virology; vol. 86; p. 2269-2274; 2005.
Hastie, Eric, et al.; "Understanding and Altering Cell Tropism of Vesicular Stomatitis Virus"; Virus Research; vol. 176; p. 16-32; 2013.
Johnson, J. E., et al.; "A Plasma Membrane Localization Signal in the HIV-1 Envelope Cytoplasmic Domain Prevents Localization at Sites of Vesicular Stomatitis Virus Budding and Incorporation in VSV Virions"; Virology; vol. 251; p. 244-252; 1998.
Saha, Manujendra N., et al.; "Formation of Vesicular Stomatitis Virus Pseudotypes Bearing Surface Proteins of Hepatitis B Virus"; Journal of Virology; vol. 79, No. 19; p. 12566-12574; Oct. 2005.
Bergman, Ira; et al. "Treatment of Implanted Mammary Tumors With Recombinant Vesicular Stomatitis Virus Targeted to Her2/neu," Int. J. Cancer, 121:425-430, Jul. 15, 2007.
Bruns; et al. "Lymphocytic Choriomeningitis Virus: VIII. Reciprocal Formation of Psuedotypes With Vesicular Stomatitis Virus," Virology 137:49-57, May 1984.
Lee et al. A Pseudotype Vesicular Stomatitis Virus Containing Hantaan Virus Envelope Glycoproteins G1 and G2 as an Alternative to Hantavirus Vaccine in Mice; Vaccine 24, 2928-2934, Apr. 5, 2006.

(56) References Cited

OTHER PUBLICATIONS

Lichty, B. D., et. al. Vesicular Stomatitis Virus: Re-Inventing the Bullet. TRENDS in Molecular Medicine, 10(5):210-216, May 2004.
Schnell, Matthias J.; et al. "Foreign Glycoproteins Expressed From Recombinant Vesicular Stomatitis Viruses Are Incorporated Efficiently Into Virus Particles," Proc. Natl. Acad. Sci. USA, 93:11359-11365, Oct. 1996.
Muik et al. "Re-engineering Vesicular Stomatitis Virus to Abrogate Neurotoxicity, Circumvent Humoral Immunity, and Enhance Oncolytic Potency," Cancer Research vol. 74 pp. 3567-3578, May 8, 2014.
Schreiber et al. "Oncolytic Chimeric Vesicular Stomatitis Virus Pseudotyped with LCMV-GP for Lung Cancer Therapy", poster shown at Annual Meeting of the Association for Cancer Immunotherapy CIMT Mainz, Germany,1 page, May 2017.
Schreiber et al. "Dominant Oncolysis in a Syngeneic Lung Cancer Model Treated with LCMV-GP-Psuedotyped Vesicular Stomatitis Virus", poster shown at Annual Meeting of the Association for Cancer Immunotherapy CIMT Mainz, Germany,1 page, May 2018.

\* cited by examiner a) 3'─[ N | rfp | M$_{ncp}$ | LCMV GP | L ]─5'
         ΔP           ΔG b) 3'─[ N | P | M$_{ncp}$ | TKgfp | L ]─5'
                    ΔG

COMPOSITIONS, METHODS AND USES FOR TREATING SOLID TUMORS USING LCMV-GP-VSV PSEUDOTYPE VECTORS

This U.S. Non-provisional application is a Continuation-in-Part application that claims priority to and the benefit of U.S. application Ser. No. 13/123,175 filed Jun. 29, 2011, which was filed as a National Stage Entry under 35 USC § 371 of PCT Application No. PCT/EP2009/007230 filed Oct. 8, 2009 which claims the benefit of DE Application No. 102008050860.8 filed Oct. 8, 2008. These applications are incorporated herein by reference in their entirety for all purposes.

Embodiments of the present invention relate to recombinant viruses derived from the vesicular stomatitis (VSV). In accordance with these embodiments, viral vectors include a gene coding for the glycoprotein GP of the lymphocyte choriomeningitis virus (LCMV). Other embodiments relate to packaging cells which produce the GP-LCMV-pseudotyped VSV virions, and the use of these virions and packaging cells for the preparation pharmaceutical compositions for treatment of solid tumors.

BACKGROUND

One key to the development of successful treatment for solid tumors is the ability to selectively and specifically kill solid tumor cells, while leaving healthy, non-tumor cells intact. Unfortunately, there are few measurable qualitative differences between neoplastic cells present in solid tumors and the healthy cells of normal tissue. Thus, treating a solid tumor inevitably results in harmful non-specific effects in a subject (e.g., neuronal toxicity). Although treatments like chemotherapy and radiation therapy have been successful for targeting solid tumors, many of the most prevalent types are resistant to these methods.

For example, malignant gliomas, the largest group of primary intracranial brain tumors, represent a therapeutic problem which is not solved yet. Although the knowledge of the biology of these tumors has grown due to intense basic research, clinical progress and prognosis are still very poor.

Malignant gliomas are tumors of neuroepithelial origin and are cytologically divided in ependimomas, oligodendrogliomas, oligoastrocytomas, astrocytomas and glioblastomas. With a proportion of more than 60%, diffuse-infiltrating astrocytomas (WHO Grade II-IV) represent the largest group of intracranial tumors. The WHO classification revised in 2001 is largely established as grading scheme for astrocytomas. According to the WHO, brain tumors are allocated by means of histological criteria to 4 malignancy grades (Kleihus and Cavenee, 2000). The prognosis for diffuse-infiltrating astrocytomas is generally poor. The prognosis depends, on the one hand, on the malignancy grade and, on the other, on the localization of the tumor and the therapy procedure. The average survival rate for patients with an astrocytoma WHO grade II is more than 5 years, with an astrocytoma WHO grade III, 2 to 5 years, and with an astrocytoma-glioblastoma of the WHO grade IV (=glioblastoma), less than 1 year.

The molecular pathogenesis of tumors is a complex process and is based on mutations of different genes which are responsible for the control of the cell cycle. Mutations in the tumor suppressor gene p53 are the most frequently found alterations in human tumors and are also responsible for the development of low-grade astrocytomas as well as for the progression to the secondary glioblastoma. However, primary developed glioblastomas very rarely have p53 mutations. A further gene, which indicates a malignant tendency of diffuse astrocytomas, is suspected to be on the long arm of chromosome 19. Further genes which are frequently altered in case of glioblastomas are the oncogenes MDM2 and MDM4 and also the tumor suppressor gene p14ARF, which are involved in the p53-dependent control of the cell cycle (Dai and Holland, 2001). An amplification of the EGF receptor gene is observed in 30-40% of the primary glioblastomas and is therefore the most frequently amplified oncogene in this tumor group (Holland, 2001). The majority of malignant gliomas responds poorly to a chemo- or radiotherapy. It is assumed that the reason for this is mutations of cell-cycle-associated genes which are also involved in the regulation of the apoptosis.

More effective therapy methods for malignant gliomas are urgently needed because from the existing therapy methods such as chemo- or radiotherapy, no significant improvements for the prognosis of the disease are to be expected. In contrast, the gene therapy of the glioblastoma offers promising possibilities which need to be exploited. A plurality of different, very effective genes was developed for this purpose. For most of them, data from experiments on animals are available (Shir and Levitzki, 2001). These therapeutic genes can be allocated to four different active principles:

(i) The gene product of so-called suicide genes converts precursors in cytotoxic molecules. An example is the thymidine kinase (TK) of the herpes simplex virus (HSV) in connection with a dosage of ganciclovir. A particular advantage is that the toxic ganciclovir triphosphate diffuses into adjacent cells, whereby a bystander effect takes place. In the last years, the activity of this enzyme was further increased. HSV TK is currently a very efficient possibility to eliminate tumor cells as well as implanted vector producing cells.

(ii) The expression of immunostimulatory cytokines such as the IL-4 can stimulate the natural defense against tumor cells.

(iii) The secretion of anti-angiogenetic proteins such as the endostatin results in a lack of blood vessels and therefore in a lack of nutrient supply in the metabolically very active tumor tissue. The tumor is virtually "starving".

(iv) Finally, a series of genes was described which engage into the signal transduction or the cell cycle of the tumor cell in order to inhibit the uncontrolled growth of these cells. However, the possibilities of use of these genes in the clinic are limited because these genes act only in the gene-modified cell itself and do not have the bystander effect as the first-mentioned active principles. This means that in order to achieve a therapeutic effect, virtually all malignant cells have to be genetically modified which is hopeless even with ideal vector systems.

One of the most important prerequisite for a successful gene therapy of the glioblastoma is provided by the multitude of existing, very effective principles of action. However, a problem which is not solved yet is the inefficient gene transfer and a poor expression of the therapeutic gene in the target cells. This is also the reason why, despite the multitude of efficient therapeutic genes, the gene therapy of glioblastoma failed in the clinic.

One advantage of the viral gene transfer over physico-chemical transfection methods is the higher gene transfer rate and the long term expression of the genes because the viruses have developed particularly efficient mechanisms to introduce their genome into cells and to express it. In particular replication-competent viruses such as, amongst others, herpes simplex virus (HSV), adenoviruses (Ad), Newcastle Disease Virus (NDV) and the vesicular stomatitis virus (VSV) are currently used as oncolytic viruses (OV). For an optimal virotherapy of glioblastoma, the OV should have the following features:

(i) They should have a tumor-specific tropism, whereby virus replication and cell lysis remains limited to the tumor tissue. This property can be enhanced by modification of the viral envelope or by using tumor-specific promoters. Since the assumption is that only a small portion of the glioma cells divide during the treatment, viruses which infect resting cells as well as proliferating cells are of advantage.

(ii) With respect to safety-relevant aspects, viruses with high genetic stability and a low toxicity outside of the tumor tissue are particularly suitable for clinical use. This allows a high virus titer and a purification of the vectors under GMP conditions. Ideally, the OV should be apathogenic for humans and should have a low infection rate among the population. An already existing immunity would result in a premature neutralization of the virus and thus would not allow an efficient therapy.

Prominent examples for oncolytic viruses in the therapy of glioblastomas are the attenuated HSV variants G207 and 1716 and the adenovirus ONYX-015. One objection against the use of oncolytic HSV for the treatment of CNS tumors is its high level replication in normal brain cells which can result in a life-threatening encephalitis. Moreover, besides potential persistence, there is the possibility of reactivation of latent HSV. The HSV variant 1716, which was generated by deleting a plurality of genes, selectively replicates in rapidly proliferating cells of the CNS but not in postmitotic neurons. Thereby, the neurotoxicity of HSV was significantly reduced. The treatment of experimental gliomas in the rat and in the mouse with HSV 1716 resulted in selective destruction of tumor cells while surrounding brain tissue remained undamaged. ONYX-015 is a further oncolytic virus which was developed for the glioblastoma therapy. Through a deletion in the E1B gene, this adenovirus is intended to selectively lyse cells with defective p53.

Oncolytic HSV as well as ONYX-015 were already clinically tested for the treatment of gliomas. Both attenuated oncolytic viruses showed a sufficient safety in clinical phase I/II studies. Independently of whether the viruses were injected intratumorally or into the resection cavity, the treatment was well tolerated and no serious side effects were observed. However, the cytolytic effects were only of transient nature, always followed by a recurrence (Cutter et al., 2206). Since normally the proliferation rate of gliomas exceeds the amplification rate and thus the spreading wave of viruses, the destruction of gliomas only by oncolysis is questionable. In fact, for an efficient treatment, the combination of a plurality of active principles is required. By using suicide genes or immunomodulatory genes in OV, a synergistic effect was demonstrated in preclinical studies (Tyminski et al., 2005; Fukuhara et al., 2005).

Besides the aforementioned DNA viruses, oncolytic RNA viruses are also under development. VSV is an enveloped negative-strand virus, the host spectrum of which includes rodents and livestock. Infections of humans are rare and are mostly asymptomatic. Due to the very low seroprevalence among the population, an impairment of the therapy efficiency by VSV-neutralizing antibodies is not to be expected. The infection and the cytoplasmatic replication of VSV take place independently of the cell cycle so that actively dividing cells and resting cells are equally infected. The efficient and preferential lysis of neoplastic cells by VSV is related to the mostly defective interferon signaling pathway and the accompanying viral replication in these cells (Wollmann et al., 2007). It was also demonstrated that independent of the cellular immune response, tumor cells with defects in the genes Myc, Ras or p53 also support the reproduction of VSV (Barber, 2004). The tumor specificity of VSV was further optimized in the last years by the preparation of recombinant viruses. The main focus here is on variants with mutation in the M protein ($\Delta$M51). This variant is not able to prevent the interferon response in healthy cells, whereby virus replication in such cells is suppressed. In tumor cells with defective IFN response, the virus can replicate and thus be selectively oncolytically active. Even after systemic application, VSV$\Delta$M51 showed a secure and efficient oncolysis of human gliomas in the mouse model (Lun et al., 2006).

The application of viral vectors directly into the brain requires a high selectivity for tumor cells and is only possible in relatively small volumes. Thus, an efficient gene transfer can only be achieved with highly concentrated vector preparations (>108/ml) which have a strongly developed tropism for glioma cells. In case of gamma-retroviral and lentiviral vectors, vector tropism and vector stability can be influenced by integrating a non-retroviral envelope protein. In many cases, the retroviral envelope protein is replaced with the more stable G-protein of VSV. A problem of these so-called pseudotyped vectors is that VSV-G is cell-toxic, namely in the producer cells as well as for the surrounding healthy tissue, which previously stood in the way of a widespread use of such VSV-G pseudotypes in the clinic.

The inefficient gene transfer in vivo and not the lack of therapeutically effective genes currently hinders successful gene therapy of the glioblastoma. The previously known vectors for gene therapy and oncolytic virotherapy of gliomas are not optimal for various reasons. The efficiency, specificity and safety of previous gene transfer methods are to be increased to such an extent that a therapeutically effective gene transfer in patients is possible.

Therefore, developing a highly potent oncolytic viral gene transfer system for the treatment of solid tumors is highly desirable.

SUMMARY

Embodiments of the present invention relate generally to methods, compositions and uses for recombinant viruses derived from the vesicular stomatitis (VSV). In accordance with these embodiments, vectors include a gene coding for the glycoprotein GP of the lymphocyte choriomeningitis virus (LCMV). Other embodiments relate to packaging cells to produce the GP-LCMV-pseudotyped VSV virions, and the use of the virions and packaging cells as part of a pharmaceutical composition for the treatment of solid tumors.

According to a further embodiment, in the VSV-LCMV-GP pseudotype vector, the envelope protein G of the VSV is replaced by GP of the LCMV (LCMV-GP).

According to a further embodiment, the vector lacks at least one gene selected from the group of n, l, p and m genes coding for proteins N, L, P and M of the VSV.

According to a further embodiment, the M protein of the VSV includes mutations which reduce the cytopathogenicity of the VSV. Examples of mutations resulting in reduced cytopathogenicity of VSV are amino acid substitutions in the 37PSAP40 region of the M protein as well as mutations M33A, M51A, V221F, S226R or their combination.

According to a further embodiment, the VSV-LCMV-GP pseudotype vector includes at least one therapeutically applicable transgene. The transgene can be a suicide gene or an immunostimulatory gene. Examples of suicide genes are genes which code for thymidine kinase of the herpes simplex virus (HSV-TK), cytosine deaminase, FKBP-FAS or FKBP-caspase 9. Examples of immunostimulatory genes are genes which code for cytokines IL-2, IL-4, IL-12, neutralizing anti-TGFbeta, or Flt3L.

According to a further embodiment, the VSV-LCMV-GP pseudotype vector includes a marker gene. The marker gene can be LacZ, an antibiotic resistance gene or a gene coding for fluorescence protein (GFP, RFP, GGP etc.).

Embodiments of the invention further include a VSV-LCMV-GP pseudotype vector system which includes at least two complementary replicating (cr) VSV vectors, wherein one vector of the vector system includes a gene gp coding for LCMV-GP, wherein the vector system further includes genes n, l, p and m coding for proteins N, L, P and M of the VSV and no functional gene coding for envelope protein G of the VSV, wherein each vector of the vector system lacks one of the genes ("complementary gene") gp, n, l, p and m, and wherein the lacking gene is present on any other vector of the vector system.

According to a further embodiment, the M protein of the VSV-LCMV-GP pseudotype vector system includes mutations which reduce the cytopathogenicity of the VSV, as illustrated above.

According to a further embodiment, the VSV-LCMV-GP pseudotype vector system includes at least one therapeutically applicable transgene and/or a marker gene, as illustrated above. The transgene/marker gene can be located on any vector of the vector system.

Embodiments of the invention further include a VSV virion pseudotyped with LCMV-GP which includes a GP protein of the LCMV as envelope protein.

Embodiment of the invention further include a virus producing cell which produces a VSV virion pseudotyped with LCMV-GP.

According to a further embodiment, the virus producing cell is an adult stem cell. The adult stem cell can be a multipotent adult progenitor cell (MAPC), a neuronal stem cell (NSC), a mesenchymal stem cell (MSC) or a BM-TIC cell (bone marrow derived tumor infiltrating cell) derived from MSC.

According to a further embodiment, the virus producing cell includes one or more expression cassettes for the expression of genes selected from the group consisting of the genes n, l, p and m coding for proteins N, L, P and M of the VSV, respectively, and a gene gp coding for LCMV-GP glycoprotein.

According to a further embodiment, the virus producing cell further includes a gene transfer vector for packaging into a VSV virion pseudotyped with LCMV-GP.

According to a further embodiment, the gene transfer vector includes a therapeutically applicable transgene and/or a marker gene, as illustrated above.

Embodiments of the invention further include an in vitro method for transferring a transgene into cell, in which method the cell is transduced with a VSV virion pseudotyped with a LCMV-GP, wherein the virion includes a transgene.

Embodiments of the invention further include an in vitro method for transferring a transgene into a cell, in which method the cell is contacted with a virus producing cell which produces a VSV virion pseudotyped with LCMV-GP, wherein the virion includes a transgene.

In some cases, the cell is a tumor cell, for example, a glioma cell.

Embodiments of the invention further include the use of a VSV-LCMV-GP pseudotype vector or a VSV-LCMV-GP pseudotype vector system of the invention for the preparation of a pharmaceutical composition for the therapy of a solid tumor.

Embodiments of the invention further include the use of a VSV virion pseudotyped with LCMV-GP for the preparation of a pharmaceutical composition for the therapy of a solid tumor.

Embodiments of the invention further include the use of a virus producing cell of the invention for the preparation of a pharmaceutical composition for the therapy of a solid tumor. In some cases, the tumor is a brain tumor, in particular, a glioma.

According to a further embodiment, at least two virus producing cells are used for the preparation of a pharmaceutical composition for the therapy of a solid tumor, wherein a first virus producing cell includes a first vector of the VSV-LCMV-GP pseudotype vector system and a second packaging cell includes a second vector of the VSV-LCMV-GP pseudotype vector system.

Furthermore, embodiments of the invention include a pharmaceutical composition which includes a VSV-LMCV-GP pseudotype vector, a VSV-LCMV-GP pseudotype vector system, a VSV virion pseudotyped with LCMV-GP, or a virus producing cell which produces a VSV virion pseudotyped with LCMV-GP. The composition can also include suitable auxiliary substances and/or carriers.

In some embodiments, the present invention relates to methods of treating a subject having one or more solid tumors, including administering to the subject a pharmaceutical composition comprising a therapeutically effective amount of a VSV-LCMV-GP pseudotype vector. In some embodiments, the VSV-LCMV-GP pseudotype vector, a gene encoding the envelop glycoprotein G of VSV, is replaced with a gene encoding the envelop glycoprotein (GP) of the lymphocytic choriomeningitis virus (LCMV). Certain embodiments of these methods can also include administration of a pharmaceutical composition comprising the VSV-LCMV-GP pseudotype vector to the subject using at least one intravenous injection or at least one intratumoral injection. In some embodiments, administration of a pharmaceutical composition further includes contacting one or more solid tumors with a therapeutically effective amount of the VSV-LCMV-GP pseudotype vector.

In some embodiments, a composition disclosed herein further includes one or more cells for producing a VSV-LCMV-GP pseudotype vector. For example, the one or more cells can include multipotent adult progenitor cells (MAPC), neuronal stem cells (NSC), mesenchymal stem cells (MSC), bone marrow derived tumor infiltrating cells (BM-TIC cells), or combinations thereof.

In some embodiments, compositions and methods of the present invention can be used to treat one or more solid tumors. For example, solid tumors of the instant application can include, but are not limited to, ovarian tumors, prostate tumors, skin tumors, lung tumors, breast tumors, liver tumors, brain tumors, CNS tumors, kidney tumors, colon tumors, bladder tumors, intestinal tumors, melanomas, gliomas, ependymomas, oligodendrogliomas, oligoastrocytomas, astrocytomas, glioblastomas, and medulloblastomas.

In some embodiments, a VSV-LCMV-GP pseudotype vector further includes one or more transgenes. For example, the VSV-LCMV-GP pseudotype vector can further include one or more transgenes encoding a suicide protein, an immunostimulatory protein, a marker protein, or combinations thereof. In some embodiments, the transgene can encode thymidine kinase of the herpes simplex virus (HSV-TK), cytosine deaminase, FKBP-FAS, or FKBP-caspase-9.

In other embodiments, the transgene can encode an interleukin protein or polypeptide or other cytokine including, but not limited to, interleukin-2 (IL-2), IL-4, IL-12, neutralizing anti-TGFβ, or Flt3L.

In some embodiments, a pharmaceutical composition disclosed herein further includes an anti-tumor agent. For example, the anti-tumor agent can be but is not limited to a chemotherapy drug, a platinum complex, a mitotic inhibitor, an alkylating agent, an anti-metabolite, an anti-tumor antibiotic, a DNA topoisomerase inhibitor, or combinations thereof.

In some embodiments, the VSV-LCMV-GP pseudotype vector can include at least one of genes n, l, p and m encoding proteins N, L, P and M. In some aspects, a composition disclosed herein can further include at least one complementary VSV vector, wherein the at least one of genes n, l, p and m is not present in the VSV-LCMV-GP pseudotype vector. In some aspects, at least one of genes n, l, p and m not present in the VSV-LCMV-GP pseudotype vector is present in the complementary VSV vector. In some embodiments, the m gene includes at least one mutation that reduces cytopathogenicity of the gene. In other embodiments, at least one of the VSV-LCMV-GP pseudotype vector or the complementary VSV vector further includes one or more transgenes encoding a suicide protein, an immunostimulatory protein, a marker protein, or combinations thereof.

In some embodiments, pharmaceutical compositions disclosed herein further includes a pharmaceutically acceptable carrier, adjuvant, excipient, or combinations thereof. Vaccine compositions disclosed herein can be administered by any method known in the art. In certain embodiments, a vaccine can be administered intradermally, intramuscularly, by inhalation, intranasally, intravenously or by any other route known in the art. Some compositions can be administered by time-release, microparticle, microgel or other formulations directly into a tumor or by indirect route as assessed by a health provider.

Other embodiments concern kits for making or using compositions disclosed herein. A kit may include constructs having VSV-LCMV-GP pseudotype vector including one or more additional modifications as disclosed herein. Other kits can include methods for making a construct contemplated herein.

DESCRIPTION OF THE FIGURES

The following drawings form part of the present specification and are included to further demonstrate certain embodiments. Some embodiments may be better understood by reference to one or more of these drawings alone or in combination with the detailed description of specific embodiments presented.

FIG. 4 is an exemplary illustration of a VSV (LCMV-GP) vector system, according to some embodiments.

DEFINITIONS

Figure 1:
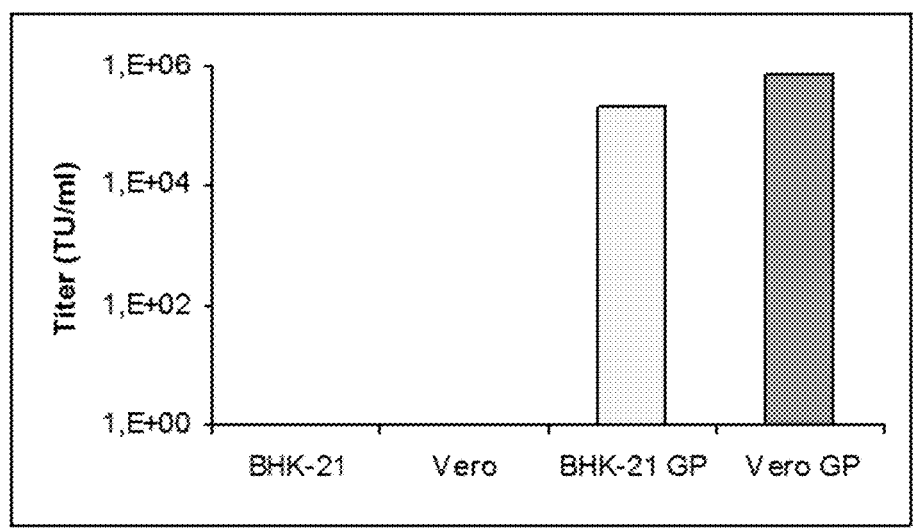
FIG. 1 is an exemplary bar graph illustrating viral titers of pseudotyped VSVgfp ncp-ΔG vectors with LCMV GP, according to some embodiments.

As used herein, "a" or "an" may mean one or more than one of an item.

As used herein, vessel can include, but is not limited to, test tube, mini- or micro-fuge tube, channel, vial, microtiter plate or container.

As used herein the specification, "subject" or "subjects" may include, but are not limited to, mammals such as humans or mammals, domesticated or wild, for example dogs, cats, other household pets (e.g. hamster, guinea pig, mouse, rat), ferrets, rabbits, pigs, horses, cattle, prairie dogs, wild rodents, or zoo animals.

As used herein, "about" can mean plus or minus ten percent.

As used herein, "treating" or "treatment" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented in that individual.

As used herein, "treat or prevent" is sometimes used herein to refer to a method that results in some level of treatment or amelioration of the disease or condition, and contemplates a range of results directed to that end, including but not restricted to prevention of the condition entirely.

As used herein, a "therapeutically effective amount" is the amount of a composition sufficient to provide a beneficial effect to the individual to whom the composition is administered.

DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

The inventors have previously developed a retroviral vector type which allows for an efficient gene transfer into glial cells of the CNS. In this new vector type, the glycoprotein GP of the lymphocyte choriomeningitis virus (LCMV) serves as viral envelope protein (Miletic et al., 1999; Beyer et al., 2002; EP 1 006 196). In comparative in vitro and in vivo tropism studies it was demonstrated that LCMV-GP pseudotypes transduce preferentially glioma cells (Miletic et al., 2004; Miletic et al., 2007). In contrast to that, VSV-G pseudotypes preferentially transduced neurons; whereas gene transfer in glioma cells was less efficient than with LCMV-GP pseudotypes. Also individual infiltrating tumor cells were efficiently transduced by LCMV-GP pseudotypes. In the rat glioma model, 90% of the rats were healed by intratumoral injection of LCMV-GP-pseudotyped lentiviral vectors (Miletic et al.; 2007b). The used vectors coded for the thymidine kinase (TK) of the herpes simplex virus, with the effect that in the transduced cells as well as in the surrounding cells, ganciclovir was converted into a cell-toxic triphosphate compound.

The selective gene transfer into gliomas, but also an efficient vector distribution within the entire tumor are decisive for the success of the therapy. Therefore, the inventors have developed tumor-infiltrating packaging cells which are supposed to release pseudotyped vectors within the entire tumor (WO 2006/008074). A promising cell type with migratory capabilities is the multipotent, adult progenitor cell which can be isolated from the bone marrow (Jiang et al., 2002). In transplantation experiments, the migration behavior of these cells was examined using the rat glioma model. It was demonstrated that the progenitor cells efficiently penetrated the tumor mass, but did not infiltrate the surrounding healthy brain tissue (Fischer et al., 2007). Conventional cell lines such as 3T3 mouse fibroblasts, Rat-1 rat fibroblasts or human 293T did not show any tumor infiltration. Rather, these cells were locally limited to the injection site or the vicinity and did not show glioma-specific migration.

In a further study, the inventors examined the therapeutic efficacy of TK-expressing progenitor cells in the rat glioma model. The result of this study was that in 70% of the rats the destruction of the tumor was solely due to the bystander effect between progenitor cell and tumor cell (Miletic et al., 2007). Moreover, the intratumoral localization of the progenitor cells by means of imaging methods was confirmed. Histological slices of the brain of treated, symptom-free rats had a cavity with a pronounced scar tissue at the location of the tumor; this indicates that the tumor in the animals was successfully eradicated by the gene therapy. Thanks to the strong expansion potential of these progenitor cells, a genetic modification with subsequent selection of individual packaging cell clones is possible. A progenitor-based packaging cell for gamma-retroviral LCMV-GP pseudotypes was developed. These packaging cells continuously produced retroviral vectors with a titer of 1-7×10E3 TU/ml. The titers remained stable over several weeks and after repeated freezing and thawing the cells (Fischer et al., 2007).

Embodiments of the invention relate to recombinant vesicular stomatitis viruses (VSV) and VSV vectors. The VSV genome includes five genes l, m, n, p and g which code for the proteins L, M, N, P and G and which are essential for the reproduction of the virus. N is a nucleoprotein which packages the VSV genomic RNA; the VSV genome can only be replicated as RNA-protein complex. L and P together form a polymerase complex which replicates the VSV genome and transcribes the VSV mRNA. M is a matrix protein which forms a kind of kit between lipid envelope and nucleocapsid and is important for particle sprouting at the cell membrane. G is the envelope protein which is incorporated in the viral envelope and is essential for the infectivity of the virus.

Embodiments of the invention include a VSV-LCMV-GP pseudotype vector and a VSV virion pseudotyped with LCMV-GP. A vector of the invention can include a gene gp coding for the GP protein instead of gene g coding for the G protein of the VSV. Accordingly, a virus/virion of the invention includes a LCMV-GP protein as envelope protein. The GP protein can be GP1 or GP2. Embodiments of the invention include-GP proteins from different LCMV strains. In some cases, LCMV-GP variants can be derived from LCMV wild-type or LCMV strains LCMV-WE, LCMV-WE-HPI, LCMV-WE-HPIopt (WO 2006/008074).

Vectors which are based on the virus of the vesicular stomatitis can have advantages over retroviral vectors in certain aspects:

(i) VSV vectors are oncolytic and have a particularly high oncolytic activity compared to other oncolytic viral vectors.

(ii) VSV vectors replicate preferentially in tumor cells and have a particularly high replication capability compared to other oncolytic viral vectors.

(iii) VSV vectors infect actively dividing cells as well as resting cells.

(iv) VSV vectors induce a strong innate humoral and cellular immune response.

(v) VSV vectors replicate purely cytoplasmatically, i.e., as RNA viruses they cannot integrate into the host cell genome or recombine into replication-competent viruses.

(vi) VSV vectors are easy to package.

(vii) The VSV glycoprotein is interchangeable with a foreign envelope protein. Examples for glycoproteins which were previously incorporated in the VSV envelope are: HIVgp160 (Owens and Rose 1993), HCVE1/E2 (Tani et al., 2007), SARS S (Ge et al., 2006) and Lassa GP (Garbutt et al., 2004).

Taken together, VSV vectors can have high therapeutic potential.

Another aspect of the VSV-LCMV-GP pseudotype vector according to the invention is a considerably reduced toxicity of the VSV viruses pseudotyped with LCMV-GP against healthy brain cells, i.e., neurons. The neurotoxicity of the VSV is attributed to the G protein of the VSV (Shinosaki et al., 2005). Actually, VSV-G pseudotypes preferentially infect normal neurons. Since neurotropism is a dose-limiting factor in all applications of oncolytic VSV, the use of the vector according to some embodiments of the present invention is that they can be used for all tumors types of solid tumors.

In addition, the VSV-LCMV-GP pseudotype vector has an increased specificity for brain tumor cells which goes back to the glioma-specific tropism of the used LCMV-GP glycoprotein and the selective transcription/replication of VSV in tumor cells. In contrast to VSV-G, the LCMV-GP envelope protein has a particular tropism for glioblastoma cells. However, the vector according to the invention can successfully be used in other tumors outside the CNS because there too the neurotoxicity of VSV, in particular in case of systemic application, is a dose-limiting factor.

Vectors pseudotyped with LCMV-GP have three crucial characteristics which non-pseudotyped vectors do not have, namely:

(i) The LCMV-GP is not cell-toxic.

(i) The LCMV-GP pseudotype vectors can be concentrated by ultracentrifugation without loss of infectivity.

(iii) The LCMV-GP pseudotype vectors show a tropism for glial cells, whereas neurons are infected inefficiently.

The invention includes replication-deficient as well as replication-competent viruses. In some cases, replication-competent virus can exhibit a high transduction. In this respect, replicable oncolytic viral vectors can be more efficient than replication-incompetent vectors.

To increase the safety during the use of replicable viruses in therapeutic uses, a vector system is provided which ensures that replication, oncolysis and the production of VSV viruses takes place only in cells which are infected by at least two replication-deficient mutually complementing vectors.

Embodiments of the invention therefore include a VSV-LCMV-GP pseudotype vector system which includes at least two complementary VSV vectors. Such complementary replicating (cr) VSV vectors can spread to a limited extent within the tumor, which increases the efficiency of the gene transfer and the oncolysis. Thus, the vector system according to the invention allows for the preparation of oncolytic VSV-LCMV-GP pseudotype vectors with limited reproduction capability for the gene transfer in gliomas and other tumors.

The principle of the vector system according to the invention is that each vector of the system lacks one of the essential genes m, n, l and p of the VSV or gp of the LCMV which, however, is present on any other vector of the system. The gene gp coding for LCMV-GP as well as possible additional genes such as therapy genes and/or marker genes can be present on any vector of the system.

Figure 5:
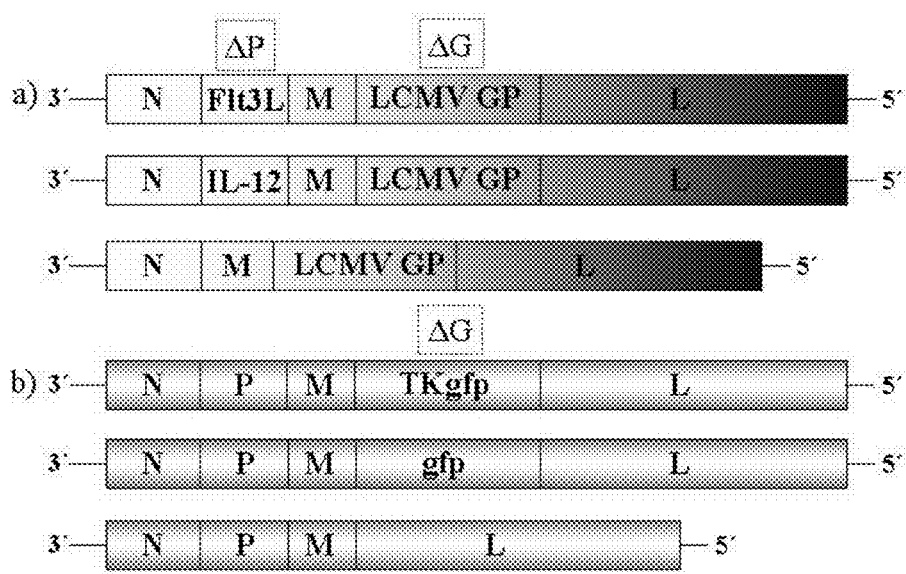
FIG. 5 is an exemplary schematic of a VSV (LCMV-GP) vector system further comprising a transgene, according to one embodiment.

Different variants of the vector system according to the invention are possible. For example, the vector system can consist of two vectors as illustrated in FIG. 5. A first vector can include GP of the LCMV instead of G of the VSV and a deletion of the gene p coding for the P protein. Also a second vector can include no VSV-G but expresses the P protein of the VSV. Each vector expresses nucleoprotein (N) and polymerase (L) of the VSV as well as a less cytopathogenic variant of the M protein (Mncp). The first vector carries in addition the marker gene rip, whereas the second vector carries the suicide gene HSV-TK and the marker gene gfp. In the variants illustrated in FIG. 6, both vectors can include a therapeutic gene, wherein the first vector can include, e.g., Flt3L or IL-12 and the second vector can include, e.g. HSV-TK.

Up to the time of this disclosure, different concepts for the therapy of the glioblastoma have been pursued: (i) the transfer of suicide genes, (ii) the elimination of the glioblastoma-related immunosuppression using immunostimulatory genes and by means of cytokine-based immunotherapy, (iii) the transfer of factors which counteract the tumor-induced angiogenesis, (iv) the use of cell cycle modulators and (v) the induction of apoptosis. For the purposes of the invention, the first three approaches (i-iii) are to be primarily considered.

In addition to their inherent oncolytic properties, the VSV-LCMV-GP pseudotype vectors and vector systems based thereon can further be improved by, for example, introducing suicide genes or/and immunostimulatory genes. Examples of suicide proteins are thymidine kinase of the herpes simplex virus (HSV-TK), cytosine deaminase, FKBP-FAS, FKBP-caspase. Examples of immunostimulatory proteins are cytokines such as IL-2, IL-4, IL-12 and Flt3L, neutralizing anti-TGFbeta. Insertions of genes with a size of up to 4.5 kb are tolerated by the VSV genome so that it would even be possible to combine two or more therapeutic genes (e.g. HSV-TK+cytokine) in one VSV genome.

In addition, the gene products exert their action also on non-infected tumor cells by means of a so-called bystander effect.

Injected viral vectors penetrate from the injection site only a few millimeters into the tumor tissue. For optimizing the vector distribution and for the targeted destruction of the tumor, tumor-infiltrating virus producing cells are used which specifically migrate in the tumor thereby releasing the viruses at the site remote from the injection site.

Virus producing cells contemplated herein include classical packaging cells for the production of virions from non-replicable vectors as well as producer cells for the production of virions from vectors capable of reproduction. Packaging cells usually include one or more plasmids for the expression of essential genes which lack in the respective vector to be packaged and/or are necessary for the production of virions.

In previous studies, packaging cells were used for transferring viral vectors; however, this involved mainly fibroblasts which do not migrate within the tumor (Short et al., 1990, Culver et al., 1992). In contrast, adult stem cells, in particular neuronal (NSC) and mesenchymal stem cells (MSC) have a high migratory potential. They remain confined to the tumor tissue, whereby a very efficient but also specific gene transfer into the tumor tissue is achieved. However, these stem cells have limited passage capacity in vitro.

A subpopulation of adult mesenchymal stem cells, so-called BM-TIC (bone marrow derived tumor infiltrating cells) infiltrate, after injection into experimentally induced gliomas, the entire tumor and, in addition, track individual tumor cells remote from the tumor mass (Miletic et al., 2007). BM-TIC are isolated from adult bone marrow, have a high expansion potential and can be used as migrating producer cells for MLV (Fischer et al., 2007) and VSV vectors.

Embodiments of the invention thus include virus producing cells which produce oncolytic VSV-LCMV-GP pseudotype vectors. In particular, these are tumor-infiltrating producer cells which release the said vectors during their migration within the tumor. Cells can include adult stem cells, in particular neuronal (NSC) and mesenchymal stem cells (MSC). In some cases, the cells are BM-TIC cells derived from MSC.

An obstacle for the preparation of a rhabdoviral virus producing cell is the cytopathogenicity of the proteins M and G. Since the G protein of the VSV is replaced by the glioma-specific and non-cytotoxic glycoprotein of the LCMV in the VSV-LCMV-GP pseudotype vectors of the invention, only the M protein remains a problem. For reducing the toxicity of the M protein in the VSV producing cell line, a non-cytopathogenic variant of the M protein can be used.

Therefore, the virus producing cells of the invention and hence also the VSV-LCMV-GP pseudotype vectors produced by said cells may include a gene coding for a mutated M protein. This vector variant is selectively oncolytic for tumor cells, whereas it is not toxic for healthy cells. M variants can have amino acid substitutions in the 37PSAP40 region of the M protein or single (M51R) or multiple (V221F and S226R; M33A and M51A) substitutions outside of the PSAP region of the M protein. For example, an M protein can have amino acid substitutions M33A, M51R, V22F and S226R. In order to ensure an efficient virus production in packaging cells, the M variant can be stably transfected with a viral interferon antagonist.

In addition, embodiments of the invention include an in vitro method for gene transfer, wherein a LCMV-GP-VSV pseudotype vector or LCMV-GP-VSV pseudotype vector system comprising a transgene is introduced into a cell either directly or by means of virus producing cells (packaging cells) according to the invention. If a cr vector system with at least two vectors is used, at least two packaging cells are used, where each of the cells produces one of the (replication-incompetent) cr vectors. The production of VSV viruses takes place only in cells which are infected with all vectors of the cr vector system and hence include all essential viral genes.

In addition, the invention relates to the use of vectors and virus producing cells according to the invention as drugs in therapeutic methods. In particular, the vectors and virus producing cells according to some embodiments of the invention are used for the therapy or treatment of solid tumors in a subject. Some of the therapeutic effect is caused by the oncolytic properties of the recombinant vectors and viruses as well as by the use of therapeutic genes.

Solid tumors can be brain tumor, liver tumor, in particular hepatocellular carcinoma, lung tumor, ovarian tumors, prostate tumors, melanomas, in particular bronchial carcinoma, and intestinal tumor, in particular colon carcinoma. Tumors can also include brain tumors, for example a glioma, in particular ependymoma, oligodendroglioma, oligoastrocytoma, astrocytoma, glioblastoma, or a medulloblastoma.

Embodiments of the invention further include a pharmaceutical composition which includes the vector, the virion, the virus producing cell of the invention and optionally additives such as carrier and auxiliary substances.

In order to increase the viral oncolysis and the transfer efficiency of the therapeutic genes, tumor-infiltrating virus producing cells which continuously release vectors are formulated for direct implantation into the tumors.

Compositions and methods of some embodiments of the present invention can be used to treat a variety of solid tumors associated with a number of different cancers. By "solid tumors" are meant tumors and/or metastasis (wherever located) other than lymphatic cancer, e.g. brain and other central nervous system tumors (e.g. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites. oligodendroglioma, oligoastrocytoma, astrocytoma, glioblastoma or medulloblastoma or other solid tumor.

Aqueous compositions of some embodiments herein can include an effective amount of a therapeutic protein, peptide, construct, epitopic core region, stimulator, inhibitor, and the like, dissolved or dispersed in a pharmaceutically acceptable carrier or aqueous medium. Aqueous compositions of vectors expressing any of the foregoing are also contemplated. In certain embodiments, the phrases "pharmaceutically or pharmacologically acceptable" refer to molecular entities and compositions that do not produce an adverse, allergic or other untoward reaction when administered to an animal, or a human, as appropriate.

Aqueous compositions of some embodiments herein can include an effective amount of a therapeutic protein, peptide, construct, an effective amount of the compound, dissolved or dispersed in a pharmaceutically acceptable carrier or aqueous medium. Such compositions can also be referred to as inocula. As used herein, "pharmaceutically acceptable carrier" can include any and all solvents, dispersion media, coatings, buffer, stabilizing formulation, antibacterial and antifungal agents, isotonic and absorption delaying agents and the like. Use of such media and agents for pharmaceutical active substances is well known in the art. Supplementary active ingredients can also be incorporated into the compositions. For human administration, preparations should meet sterility, pyrogenicity, and general safety and purity standards as required by FDA Office of Biologics standards.

In certain embodiments, biological material should be extensively dialyzed to remove undesired small molecular weight molecules and/or lyophilized for more ready formulation into a desired vehicle, where appropriate. The active compounds or constructs will then generally be formulated for parenteral administration, e.g., formulated for injection via the intravenous, intramuscular, sub-cutaneous, intralesional, intranasal or even intraperitoneal routes. Any route used for vaccination or boost of a subject can be used. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and certain storage parameters (e.g. refrigeration and freezing) and must be preserved against the contaminating action of microorganisms, such as bacteria and fungi.

If formulations or constructs disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents known in the art. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds or constructs in the required amount in the appropriate solvent with various of the other ingredients enumerated above, as required, followed by filtered sterilization.

Upon formulation, solutions can be administered in a manner compatible with the dosage formulation and in such amount as is therapeutically effective. The formulations are easily administered in a variety of dosage forms, such as the type of injectable solutions described above, but slow release capsules or microparticles and microspheres and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intratumorally, intramuscular, subcutaneous and intraperitoneal administration. In this context, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion.

The term "unit dose" refers to physically discrete units suitable for use in a subject, each unit containing a predetermined quantity of the construct composition or boost compositions calculated to produce desired responses, discussed above, in association with its administration, e.g., the appropriate route and treatment regimen. The quantity to be administered, both according to number of treatments or vaccinations and unit dose, depends on the subject to be treated, the state of the subject and the protection desired. The person responsible for administration will, in any event, determine the appropriate dose for the individual subject. For example, a subject may be administered a construct composition disclosed herein on a daily or weekly basis for a time period or on a monthly, bi-yearly or yearly basis depending on need or exposure to a pathogenic organism or to a condition in the subject (e.g. cancer).

In addition to the compounds formulated for parenteral administration, such as intravenous, intratumorally, intradermal or intramuscular injection, other pharmaceutically acceptable forms include, e.g., tablets or other solids for oral administration; liposomal formulations; time release capsules; biodegradable and any other form currently used.

One may also use intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 7.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines and are used for asthma prophylaxis.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will include an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Further embodiments disclosed herein can concern kits of use with methods and compositions. Some embodiments concern kits having vaccine compositions of use to reduce onset of or treat subjects having one or more solid tumors. Other embodiments can concern kits for making and using molecular constructs described herein. Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the constructs, vaccine compositions and any other reagent containers in close confinement for commercial sale. Such containers may include injection or blow-molded plastic containers into which the desired vials are retained. Optionally, one or more additional agents such as other anti-viral agents, anti-fungal or anti-bacterial agents may be needed for compositions described, for example, for compositions of use as a vaccine.

Dose ranges used during vaccination can vary depending on the nature of the viral vector used and the solid tumor. Frequency of dosing can vary depending on the nature of the solid tumor and also the route of administration used. In some embodiments of the present invention, VSV-LCMP-GP pseudotyped vector compositions can be administered to a subject at a dose ranging from about $1\times10^5$ PFU to about $1\times10^{15}$ pfu (plaque forming units), depending on mode of administration, the route of administration, and the nature of the solid tumor and condition of the subject and specifics regarding the tumor, for example. In some cases, a VSV-LCMP-GP pseudotyped vector compositions can be administered at a dose ranging from about $1\times10^8$ pfu to about $1\times10^{15}$ PFU. In other cases, a VSV-LCMP-GP pseudotyped vector compositions can be administered at a dose ranging from about $1\times10^{10}$ PFU to about $1\times10^{15}$ pfu. In other cases, a VSV-LCMP-GP pseudotyped vector compositions can be administered at a dose ranging from about $1\times10^8$ pfu to about $1\times10^{12}$ pfu. A more accurate dose can also depend on the subject in which it is being administered. For example, a lower dose may be required if the subject is juvenile, and a higher dose may be required if the subject is an adult human subject. In certain embodiments, a more accurate dose can depend on the weight of the subject. In certain embodiments, for example, a juvenile subject can receive about $1\times10^8$ PFU and about $1\times10^{10}$ pfu, while an adult human subject can receive a dose between about $1\times10^{10}$ pfu and about $1\times10^{12}$ pfu.

Compositions disclosed herein may be administered by any means known in the art. For example, compositions may include administration to a subject intravenously, intratumorally, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a cream, or in a lipid composition.

Any method known to one skilled in the art may be used for large scale production of recombinant VSV vectors and vector constructs, such as LCMV-GP-pseudotyped vectors. For example, master and working seed stocks may be prepared under GMP conditions in qualified primary CEFs or by other methods. Cells may be plated on large surface area flasks, grown to near confluence and infected at selected MOI and vaccine virus purified. Cells may be harvested and intracellular virus released by mechanical disruption, cell debris removed by large-pore depth filtration and host cell DNA digested with endonuclease. Virus particles may be subsequently purified and concentrated by tangential-flow filtration, followed by diafiltration. The resulting concentrated bulk vaccine may be formulated by dilution with a buffer containing stabilizers, filled into vials, and lyophilized. Compositions and formulations may be stored for later use. For use, lyophilized vaccine may be reconstituted by addition of diluent.

Certain anti-cancer or anti-tumor agents of use in compositions and methods disclosed herein can be administered by any means known in the art. by Compositions as disclosed herein can also include adjuvants such as aluminum salts and other mineral adjuvants, tensoactive agents, bacterial derivatives, vehicles and cytokines. Adjuvants can also have antagonizing immunomodulating properties. For example, adjuvants can stimulate Th1 or Th2 immunity. Compositions and methods as disclosed herein can also include adjuvant therapy. For example, adjuvant therapy can include chemotherapy, hormone therapy, radiation therapy, immunotherapy, and targeted therapy, or combinations thereof.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Example 1: Transduction of Glioma Cells by LCMV-GP-Pseudotyped Vectors

Defective VSV vectors which code GFP but no viral envelope protein (VSVgfp-ncp-ΔG) were transduced into BHK-21 and vero cells which in turn stably express the GP of LCMV. 1×10E5 cells (BHK-21, -GP, vero, -GP) were sown per 24-well plate cavity and four hours later transduced at MOI=5 with VSVgfp-ncp-ΔG vectors. 24 hours later, the culture supernatant was collected and the titer in BHK-21 was determined by means of FACS analysis of the GFP expression. FIG. 1 shows that the transduced cells produced LCMV-GP-pseudotyped VSV vectors, wherein depending on the used cell type, the pseudotype titers varied between 2-7×10E5 TU/ml.

Figure 2:
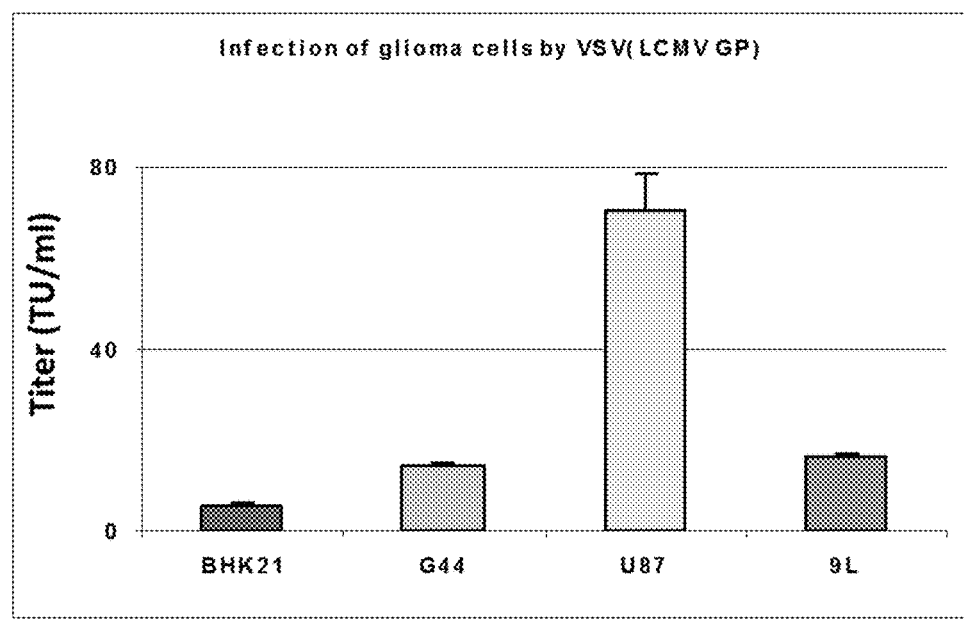
FIG. 2 is an exemplary bar graph illustrating transduction of glioma cell lines with VSV (LCMV GP) vectors, according to some embodiments.

Since the pseudotypes were intended for the gene transfer in gliomas, the transduction efficiency of the vectors was checked for different glioma cell lines. Two human glioma cell lines (U87, G44) and a rat glioma cell line (9L) were tested. BHK-21 were used again as a control. 1×10E5 cells per 24-well plate cavity were seeded and four hours later transduced at MOI=0.3 (titration on BHK-21) with VSV-LCMV-GP pseudotype vectors. 24 hours later, the percentage of GFP-expressed cells was determined by FACS and the titer was calculated therefrom. FIG. 2 shows that the glioma cell lines were efficiently transduced by LCMV-GP-pseudotyped VSV vectors.

Figure 3:
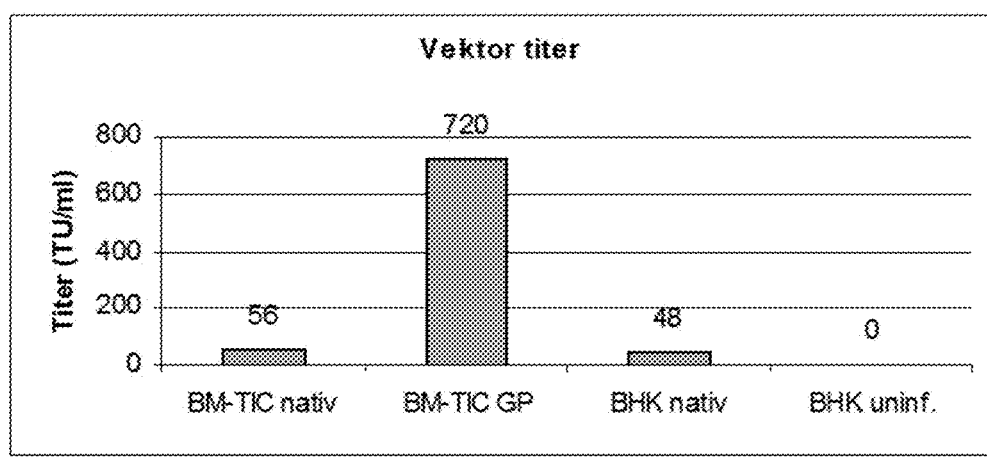
FIG. 3 is an exemplary bar graph illustrating viral titers of pseudotyping of VSVgfp ncp-ΔG vectors with LCMV GP in BM-TIC, according to some embodiments.

Example 2: Packaging of VSV-LCMV-GP Pseudotype Vectors in Multipotent Progenitor Cells The inventors have already demonstrated that stem cells which were isolated according to the protocol of C. Verfaillie (Jiang et al., 2002), have tumor-infiltrating properties. Because only their migration potential but not their differentiation potential was examined, these cells were called BM-TIC (bone marrow derived tumor infiltrating cells). For testing the packaging capability of BM-TIC for VSV vectors, LCMV-GP-expressing BM-TIC were transduced with the defective VSV-GFP vector. 1×10E5 cells (BM-TIC, -GP, BHK-21) were seeded per 24-well plate cavity and four hours later transduced at MOI=5 with VSVgfp-ncp-ΔG vectors. 24 hours later, the culture supernatant was collected and titrated on BHK-21 cells. FIG. 3 shows that VSV-LCMV-GP pseudotypes can also be prepared in BM-TIC. However, the titers are lower as for example with BHK-21 cells (see FIG. 1).

Example 3: Development of Complementary Replicating (Cr) VSV-LCMV-GP Pseudotype Vectors A high transduction rate can be achieved with viruses capable of reproduction. In order to increase the gene transfer rate in gliomas and at the same time to ensure a high degree of safety, a VSV pseudotype vector was established which is replication-competent to a limited extent. Systems with complementary defective viruses have been described for retroviruses (Trajecevski et al., 2004) and different flaviviruses (Riepl & Mandl, 2007). The principle of such systems is to distribute the viral genome between two incomplete replicons. Infectious viruses are only produced if one and the same cell is infected with both vectors and only through this co-infection includes all the necessary components for packaging the virus genome.

Figure 4:
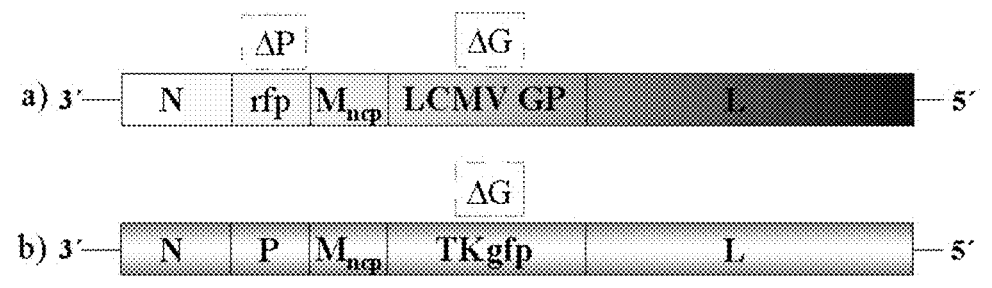

FIG. 4 shows an example of complementary vectors of the vector system according to the invention. For an efficient replication and packaging, the first vector lacks the phosphoprotein P. In order to be able to determine the viral titer of these vectors in a simpler manner, the vector encodes the red fluorescent protein (rfp) instead of P. The lacking P function is complemented during the co-infection of the cell by the second vector. However, the latter alone is not capable of reproduction because it lacks the essential envelope protein VSV-G. By means of this vector, therapeutic genes are applied.

While only the genomic RNA of positive-strand RNA viruses is infectious, negative-strand RNA viruses such as the VSV need in addition to the viral RNA genome at least viral nucleoprotein (N) and viral polymerase (L) in order to generate an infectious virion from cloned viral cDNAs. The system for preparing recombinant VSV is based on the cytoplasmatic expression of viral (+)RNA and the viral proteins N, P and L using the T7-RNA polymerase which is constitutively expressed in BSR T7/5 cells. In order to prepare the desired vectors, genomic constructs together with the expression plasmids for N, P and L and additionally the expression plasmid for VSV-G in the case of Vector b) (FIG. 4) are co-transfected into the BSR T7/5. The titers can be considerably increased by passaging the viruses obtained in this manner on cells which express the lacking component in trans. For the LCMV-GP-deficient vector, a BHK-21 cell line which stably expresses GP was established. For the P-deficient vector, a BHK-21 cell line which expresses the P protein was established.

Preparation and Characterization of Cr LCMV-GP Pseudotype VSV Vectors

After characterization of the individual vectors with respect to their titer and their transduction efficiency, the spread of the vectors in vitro is examined. For this, BHK-21 cells are co-infected with both vectors and the replication and thus the generation of new vectors by serial passage of the culture supernatant on native BHK-21 is examined. These experiments are repeated with different glioblastoma cell lines (G44, G62, U87) which are cultivated as monolayer as well as spheroids.

Tumor spheroids are three-dimensional, organoid cell groups which reflect the nature and heterogeneity of tumors better than monolayer cultures. The actively dividing tumor cells are located in a loose formation at the edge of the cell aggregate, whereas cells located deeper inside no longer divide and a formation of necrotic areas takes place here (Carlson et al., 1984). Experiments with spheroids provide information about intratumoral transduction efficiency, the spreading kinetics and the oncolytic effect of the cr VSV-LCMV-GP pseudotype vector system. These spheroids thus allow an initial optimization of the system without the need of conducting experiments in animals. A possible toxicity of the cr LCMV-GP-pseudotyped VSV vectors, the therapeutic effectiveness of the oncolysis and the presence of the remaining viruses after tumor elimination are examined in the animal model (see example 6).

The viral RNA polymerase has no recombinase activity and there are also no cellular recombinases in the cytoplasm so that the recombination between two negative-stranded RNA viruses can only take place by a template switching of the RNA polymerase. However, this is an extremely rare event (Finke & Conzelmann, 2005; Spann et al., 2003). The generation of a recombinant, replicable VSV represents a safety risk and is examined. For this, viral RNA is isolated at different times from the culture supernatant of co-infected cells and examined with a transgene-specific (e.g. gfp) probe in Northern blots. If RNA species with "excess length" are detectable, the viruses from the supernatant are plaque-purified and examined by means of standard methods with respect to their infectivity and are subsequently characterized by means of molecular biology.

Example 4: Establishment of a Migrating Producer Cell for the Preparation of Therapeutically Effective VSV (LCMV-GP) Pseudotype Vectors Migrating VSV-LCMV-GP producer cells are established for cr VSV vectors and for replication-competent VSV-LCMV-GP vectors.

Preparation and Characterization of Different M Variants

The VSV M protein has two essential tasks within the VSV cycle. On the one hand, it is essential as structural component of the virion for the assembly and the sprouting of the viruses. On the other hand, it contributes significantly to the viral pathogenesis through its "host shut-off" activity directed to the host protein synthesis and through induction of the apoptosis. In this connection, an important function of M is the inhibition of the nucleo-cytoplasmatic transport of IFN mRNA. Thereby, the first defense mechanism of the cell against viral infection is suppressed.

Due to this strong cytotoxic effect, it is not possible to express the M protein in cell lines on a long-term basis. However, a plurality of mutations in the M protein is known which result in the attenuation of the virus. Irie and coworkers demonstrated that by amino acid substitutions in the so-called 37PSAP40 region of the M protein, a VSV mutant with greatly reduced cytopathogenicity was created (Irie et al., 2007). Furthermore, as illustrated in mouse experiments, M variants with single (M51R) or multiple (V221F and S226R; M33A and M51A) mutations outside of the PSAP region are also greatly attenuated (Desforges et al., 2001; Jayakar and Whitt, 2002). These viruses are not able to suppress the release of IFN-α/β and accordingly induce an antiviral status which protects the animals against an infection. However, in tumors which often have defects in the IFN system, these viruses can reproduce and lyse the tumor. For safety reasons, such attenuated variants are of particular importance for the gene therapy because they replicate preferentially in tumor cells.

Also, the inventors have cloned a non-cytopathogenic variant of the M protein (Mncp) which includes the mentioned mutations M33A, M51R, V221F and S226R and is no longer able to suppress the synthesis of IFN-β. This variant replicates in a similar efficient manner as the parent virus on IFN-incompetent cells, but is attenuated on IFN-competent cells. To ensure efficient virus production in BM-TIC, the cells are stably transfected with a viral interferon antagonist (Haller et al., 2006).

Preparation and Characterizing of a BM-TIC-Derived Producer Cell for VSV-LCMV-GP Pseudotype Vectors Tumor cells are primarily transduced due to the glioma-specific tropism of the VSV-LCMV-GP pseudotypes. Therefore, it is possible to also work with M variants which still show certain cytopathogenicity. In order to keep the toxic effects in BM-TIC low, the antiviral MxA protein should be expressed in the cells via a Tet-inducible promoter. Retroviral vectors with Tet-inducible promoter are known (Löw et al., 2006). The Tet-responsive element (tTA) is also introduced into BM-TIC via a retroviral vector. MxA is an interferon-induced GTPase with antiviral activity towards RNA viruses (Pavlovic et al., 1992; Stäheli and Pavlovic, 1991). In the cytoplasm it is present in the form of large oligomers, is not toxic and inhibits the replication of VSV by a hitherto unknown mechanism. LCMV-GP expressing BM-TIC are transduced with the Tet-regulated MxA and the tTA vector and subsequently infected with the VSV vectors. As long as the antibiotic is present in the medium, the cells are resistant against a productive infection with VSV (LCMV-GP) due to the presence of MxA. Only during the in vivo application, the antibiotic is removed and a viral replication and production of VSV (LCMV-GP) gradually begins. Since MxA with a half-life of two days is very stable, the mutant MxA(L612K) can alternatively be used. MxA(L612K) inhibits the infection of VSV with the same effectiveness as the wild-type protein, but is not able to form oligomers. Hereby it is destabilized and has a short half-life of only two hours (Janzen et al., 2000).

Both producer cells, BM-TIC which produce vectors with non-cytopathogenic M as well as BM-TIC which are protected against VSV-related lysis through MxA expression, are characterized as follows:

(i) The vector titers and the duration of the vector production are determined.

(ii) The influence of freezing and thawing of the cells on the vector titer is analyzed.

(iii) Whether the cells still have tumor-infiltrating properties and which transduction efficiencies are achieved in the tumor tissue is analyzed first in the spheroid model and subsequently in the animal model.

(iv) The produced vector supernatant is checked for the presence of replicable VSV.

Example 5: Cloning and Packaging of Therapeutic Genes

A suicide gene can be used as therapeutic gene according to the invention. An example of such a gene is the thymidine kinase of the herpes simplex virus (HSV-TK) with the most experience in the clinic. Through the constitutive expression of the HSV-TK, packaging cells and transduced cells can be reliably eliminated at the end of the therapy so that no danger can arise from mitotically active packaging cells.

For the immunotherapy of malignant gliomas, i.e., for strengthening the poorly developed local immune response in the brain, immunomodulatory genes can be used. Examples of such genes are cytokines, in particular IL-12 and Flt3L. After antigen stimulation, IL-12 is naturally secreted by antigen-presenting cells such as dendritic cells, macrophages and B cells and mediates a strong Th1-based anti-tumor immune response. It enhances the growth and the differentiation of naive T cells into Th1 cells and thus counteracts a glioma-induced suppression of the T cell proliferation and IFN-gamma production. IL-12 enhances the cytotoxic activity of natural killer and CD8+ cells and has in addition an anti-angiogenic activity (Majewski et al., 1996). In a plurality of animal models, the effectiveness of an IL-12-mediated immune response against gliomas has already been demonstrated in an impressive manner (Toda et al., 1998; Kikuchi et al., 1999). The cytokine Flt3L is essential for the proliferation and differentiation of antigen-presented dendritic cells and thus seems to be particularly well suited for the purposes of a gene therapy. Sumia and colleagues observed in the rat/mouse a strong local influx of dendritic cells after i.c. transduction of gliomas with the Flt3L gene. 70% of the treated rats showed tumor regression and survived.

The combination of a cytokine with a suicide gene (TK) does not only offer maximum safety, but also allows a successful therapy with low transduction efficiency due to the bystander effect. This approach combines three active principles, namely viral oncolysis, suicide gene-induced apoptosis and local immunostimulation in order to increase the efficiency of the gene therapy of the glioblastoma.

First, Il-12 and Flt3L are cloned into the VSV vectors. IL-12 is species-specifically active so that the murine IL-12 has to be used for testing in the rat glioma model. In contrast, more than 70% of human and murine Flt3L are homologous and are cross-reactive in both species. The immunostimulatory genes are cloned into the position of the p gene, whereas TKgfp or gfp on the second vector replaces the VSV-G gene. The following gene combinations are cloned into the two vectors of the cr VSV-LCMV-GP pseudotype vector system (FIG. 5):

1) vector a=IL12 or Flt3L+vector b=TKgfp (or TK)
2) vector a=IL12 or Flt3L+vector b=gfp
3) vector a=IL12 or Flt3L+vector b=empty
4) vector a=empty+vector b=TKgfp (or TK)
5) vector a=empty+vector b=gfp
6) vector a=empty+vector b=empty After cloning, glioma cell lines and BM-TIC are transduced and the concentration of the cytokine contained in the supernatant is verified by ELISA. For the production of physiologically relevant amounts the vectors are concentrated via ultracentrifugation. The vectors are first used for the transduction of spheroids and their competence to bystander killing is examined in this system. Afterwards, the vector supernatants together with the prepared packaging cells are sent to Bergen to our cooperation partner. There, the in vivo testing in the syngeneic rat glioma model takes place. The survival rate of the treated rats after ganciclovir application is evaluated. At the same time, the therapeutic effectiveness of the immunotherapy in the absence of TK is examined. The vector combination 6) provides information about the effectiveness of the oncolysis. Tumor size and thus the therapy success are monitored via MRI and PET (Miletic et al., 2007). The effect of the immunomodulatory genes is evaluated by means of immunohistochemical methods for detection of infiltrate cells. As described in the following paragraph, the therapeutic approach is also examined in the human glioma model.

Example 6: Testing of the Therapeutic Active Principle in Two Glioma Models

The recombinant VSV vectors are first characterized in vitro and are subsequently investigated in the animal model for their effectiveness. For this purpose, two particularly meaningful rat models are used.

A syngeneic 9L rat glioma model is used for the examination of immunological aspects and the carrying out of immunotherapeutic methods. For this purpose, glioma cell lines are implanted into the brains of Fisher rats which subsequently develop tumors within a few days. 9L gliosarcoma cells which were isolated from Fisher rats served as tumor cell lines. Various vectors or cell lines are then stereotactically injected into the induced tumors. This rat model has the following characteristics:

It represents a well reproducible system with a low inter-individual variance.

(ii) The tumors have characteristics similar to human gliomas such as, e.g., the invasive and aggressive growth behavior as well as the production of TGFβ2 as immunosuppressive factor.

(iii) In contrast to the SCID/nude mouse model or the rat xenograft model, the system allows the examination of immunological aspects or the testing of immunotherapeutic methods.

A human glioma model in nude rats is used for testing the oncolytic activity of the vectors and cells according to the invention towards human glioma cells. The rat xenograft model simulates various growth characteristics of human gliomas. Not a defined glioblastoma cell line but primary tumor material from patients is used here for establishing the tumor, which allows to simulate the heterogeneity within human gliomas (Sakariassen et al., 2006). By the serial passage of human gliomas in nude rats, different phases of the malignant tumor development can be mapped and the therapy success can be examined. The human glioma model is particularly well suited for the examination of therapeutic approaches because it has the following characteristics:

(i) The tumors have similar characteristics to human gliomas such as, e.g., the invasive and aggressive growth behavior. Not a glioma cell lines but primary patient material is used for establishing the tumors.

(ii) Through the serial passage of tumors, different phases of the development of a malignant tumor can be mapped and the success of therapy can be verified. Tumors of the first generation grow slowly, are highly invasive and have a low neurovascularization. A greatly vascularized phenotype with strong proliferation and reduced invasion develops through passaging.

(iii) The cellular phenotype of highly invasive, non-angiogenetic gliomas is similar to the one of tumor stem cells. Thus, this animal model allows the testing of the therapeutic effectiveness of our concept on the stem cell component of the human GBM.

Two categories of tumors can be distinguished:

(i) Early tumors with a slow, highly invasive growth behavior. These tumors have only a low vascularization.

(ii) Late tumors which are well supplied with blood and grow fast. This phenotype is poorly invasive.

The human glioma model is very well suited for examining suicide gene therapy as well as the viral oncolysis. However, up to now there are no animal models for the human glioblastoma which can be used for the analysis of the immunotherapeutic effectiveness of gene therapeutic methods.

The success of therapy is analyzed and evaluated by means of imaging methods and finally with histological techniques. First, the mode of action of the complementary replicating VSV(LCMV-GP) pseudotypes is examined by intratumoral injection of concentrated vector supernatants in the rat glioma model. The transduction efficiency and the distribution of the gfp-coding vectors within the tumors are examined after a few days by means of a fluorescence microscopic analysis of frozen sections. Furthermore, oncolysis and the invasion of immune cells are immunohistochemically evaluated. As a supplement, the effectiveness is also examined in the animal model for the human glioblastoma.

In the same model, the migration capability of the BM-TIC producer cells and the infectivity of the produced VSV vectors are examined. For this purpose, the cells are stained with a green dye whereas the released vectors code for rip. This approach allows a simple fluorescence-based differentiation between BM-TIC and transduced tumor cells.

Finally, the therapeutic efficiency of the individual transgene-coding pseudotypes is compared. For this purpose, the packaging cells and also the concentrated vector supernatants are injected into established 9L tumors. The vectors include an immunostimulatory gene in combination with TK. Ganciclovir administration begins a few days after the stereotactical application of the vectors or the packaging cells. The therapeutic efficiency of the immunomodulatory component of the vector is evaluated in animals that receive vectors containing only TK. Upon completion of the treatment, the effectiveness of the individual therapy concepts is evaluated based on the tumor size with imaging methods (MRI; PET). A portion of the brains of rats treated with immunotherapy is used for characterizing the immune status. The expression of MHC molecules and the distribution of T cells, granulocytes, macrophages and microglial cells are examined on the frozen sections by immunohistochemical methods. In addition, the quantity and phenotypical composition of the i.c. infiltrate cells are analyzed by flow cytometry. The formulation with the best therapeutic effect is adapted for the treatment of human gliomas. Such a prototype could be transferred directly into preclinical safety studies and, after establishing the respective methods for GMP production, into clinical studies.

Example 7: Treatment of Melanoma

Figures 6A, 6B:
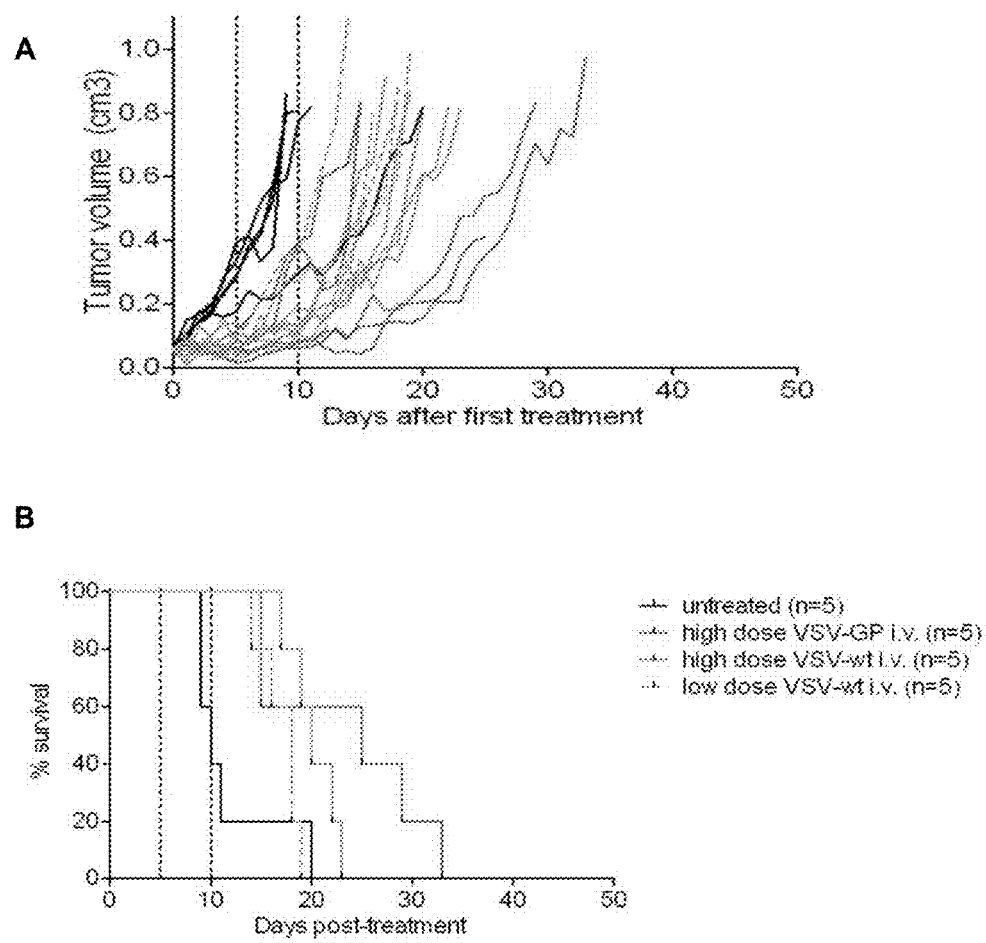
FIGS. 6A-6D are exemplary illustrations of some methods of use of VSV (LCMV-GP) to treat melanoma, according to one embodiment.
Figure 6C:
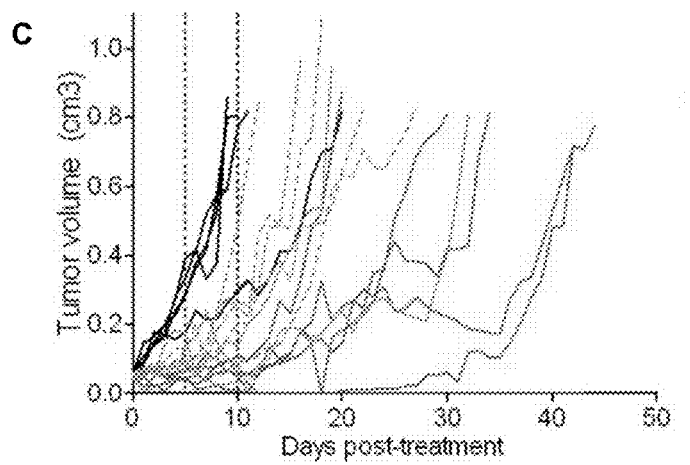
Figure 6D:
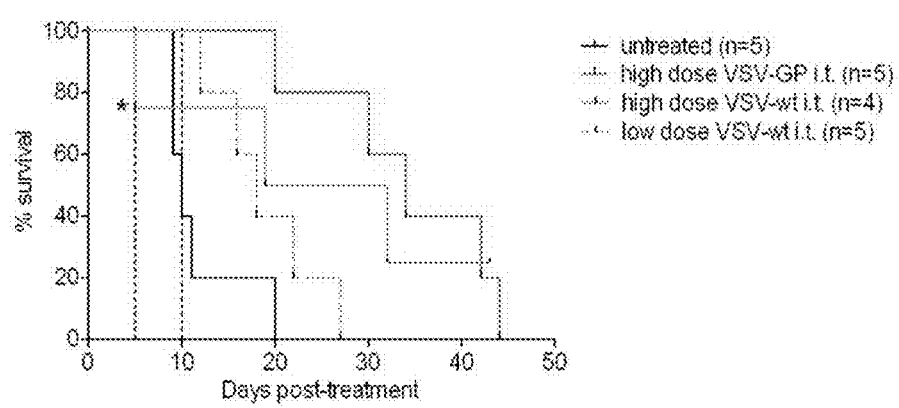

FIGS. 4 and 5 illustrate exemplary embodiments of pseudotyped viral vector constructs, as disclosed herein. In some exemplary methods, experiments were conducted to test the anti-tumor efficacy of VSV-LCMV-GP in a syngenic subcutaneous melanoma mouse model. C57BL/6 mice were transplanted subcutaneously (s.c.) with $5\times10^5$ murine B16ova melanoma cells and treated first with intratumoral (i.t.) injections of $1\times10^8$ PFU VSV-LCMV-GP (high-dose), $1\times10^8$ PFU VSV-wt (high-dose) or $1\times10^6$ PFU VSV-wt (low-dose) when tumors reached 0.05 cm$^3$ or left untreated as a control. As illustrated in FIGS. 6A-6B, mice were then treated by intravenous (i.v.) injection of $1\times10^7$ PFU VSV-LCMV-GP (high-dose), $1\times10^7$ PFU VSV-wt (high-dose) or $1\times10^5$ PFU VSV-wt (low-dose) at day 5 and again at day 10. As illustrated in FIGS. 6C-6D, mice were treated by i.t. injection of $1\times10^8$ PFU VSV-LCMV-GP (high-dose), $1\times10^8$ PFU VSV-wt (high-dose) or $1\times10^6$ PFU VSV-wt (low-dose) at day 5 and again at day 10. Animals were monitored for tumor growth and survival in the presence or absence of the construct. ("*" in FIG. 6D denotes a mouse that was sacrificed due to signs of neurotoxicity).

Exemplary results illustrated in FIGS. 6A-6D indicated that both VSV-LCMV-GP and VSV-wt therapy suppressed tumor growth and resulted in prolonged survival after intratumoral as well as after intravenous administration. However, regardless of the method of administration, tumor growth in mice treated with VSV-LCMV-GP was significantly attenuated compared to tumor growth in mice treated with VSV-wt. Mice treated with VSV-LCMV-GP survived longer compared to mice treated with VSV-wt. Additionally, intravenous treatment was more efficient for VSV-LCMV-GP than for VSV-wt upon repeated virus application, perhaps due to the induction of high levels of neutralizing antibodies against VSV-wt after the first treatment, which reduced efficacy of subsequent VSV-wt injections. This effect did not appear to be present in VSV-LCMV-GP mice.

Experiments were also conducted to determine the anti-tumor effect of VSV-LCMV-GP on melanoma metastases in the lung. Wild-type C57BL/6 mice were intravenously injected with $1 \times 10^6$ B16 ova melanoma cells. At day 2, 4, 6, 8, and 10 post-injection the animals were treated with $5 \times 10^8$ PFU VSV-LCMV-GP or left untreated as a control (n=8 animals per group). Four days after the last treatment (i.e., on day 14), the animals were sacrificed and the lungs examined visually for B16ova metastases.

Figure 7A:
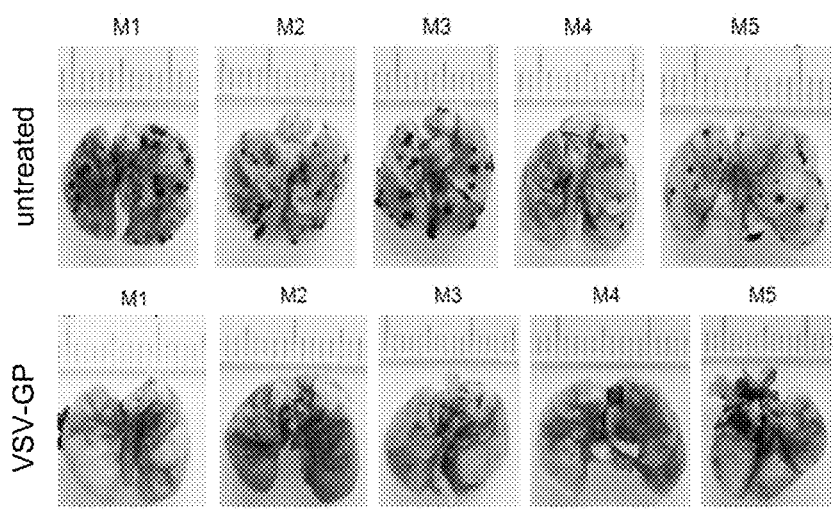
FIGS. 7A-7B are exemplary illustrations of some methods of use of VSV (LCMV-GP) to treat melanoma that metastasizes to the lung, according to one embodiment.
Figure 7B:
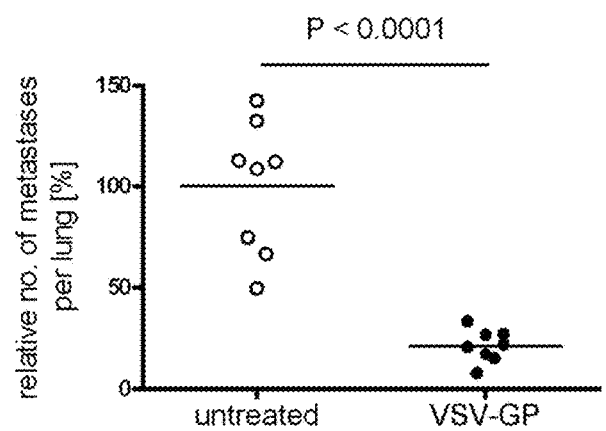

FIG. 7A includes images from five representative lung samples, M1 though M5, from mice treated with VSV-LCMV-GP and untreated controls. Animals treated with VSV-LCMV-GP exhibited few and smaller metastases compared to controls. FIG. 7B is a graphical representation illustrating that all VSV-LCMV-GP treated animals (solid circles) showed significantly fewer metastases compared to controls (open circles) ($p<0.0001$).

The anti-tumor efficacy of VSV-LCMV-GP was demonstrated in both a syngenic and in a xenograft subcutaneous melanoma mouse model, as described above. Both local (intratumoral) and systemic (intravenous) virus injections suppressed tumor growth and prolonged survival of the mice. Additionally, using an optimized treatment schedule, 3 of 5 mice were free from syngenic subcutaneous tumors, and were protected from tumor development upon re-transplantation of tumor cells. Thus, prolonged protection was observed. Moreover, intravenously administered VSV-LCMV-GP was highly efficient in a melanoma lung metastasis model.

Example 8: Treatment of Ovarian Tumors

Figure 8A:
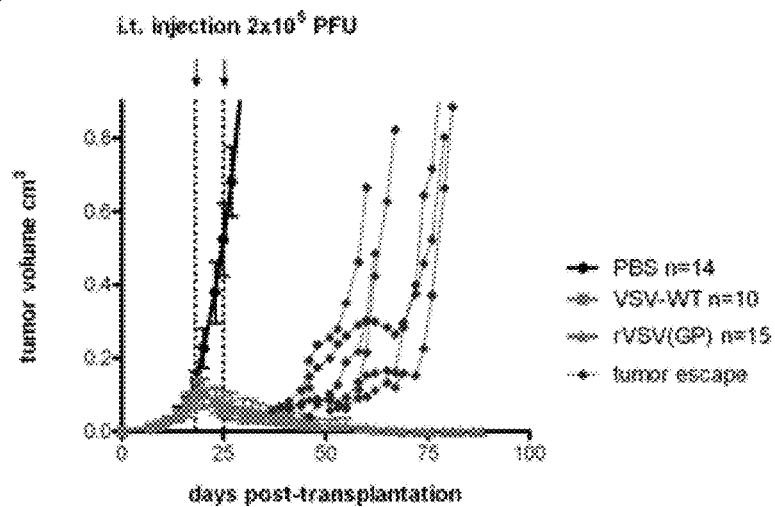
FIGS. 8A-8D are exemplary illustrations of some methods of use of VSV (LCMV-GP) to treat of ovarian tumors, according to one embodiment.
Figure 8B:
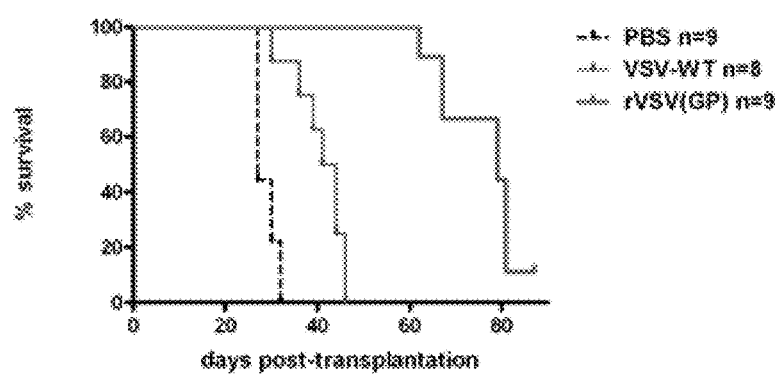

Experiments were conducted to determine the anti-tumor effect of VSV-LCMV-GP (also referred to as "recombinant VSV(GP)" or "rVSV(GP)") on ovarian tumors using a subcutaneous xenograft model of ovarian cancer in mice. Corresponding to FIGS. 8A-8D, $5 \times 10^6$ A2780 cells were injected subcutaneously (s.c.) into both flanks of NOD/SCID mice. Tumors were treated at a size of 0.1 cm³ with i.t. injection of PBS, $2 \times 10^5$ PFU VSV-wt, or $2 \times 10^5$ PFU rVSV-GP. Animals were monitored for tumor growth and survival. Tumor growth was measured using a sizing caliper. At a tumor size of 0.8 cm,³ mice were sacrificed. Data points represent mean±SD. FIG. 8A demonstrates that in all cases, VSV-LCMV-GP treatment led to a reduction in tumor size and attenuated tumor growth, as compared to both VSV-wt treatment and untreated controls. Additionally, FIG. 8B illustrates that mice treated with VSV-LCMV-GP exhibited significantly prolonged survival compared to both VSV-wt treatment and untreated controls.

Figure 8C:
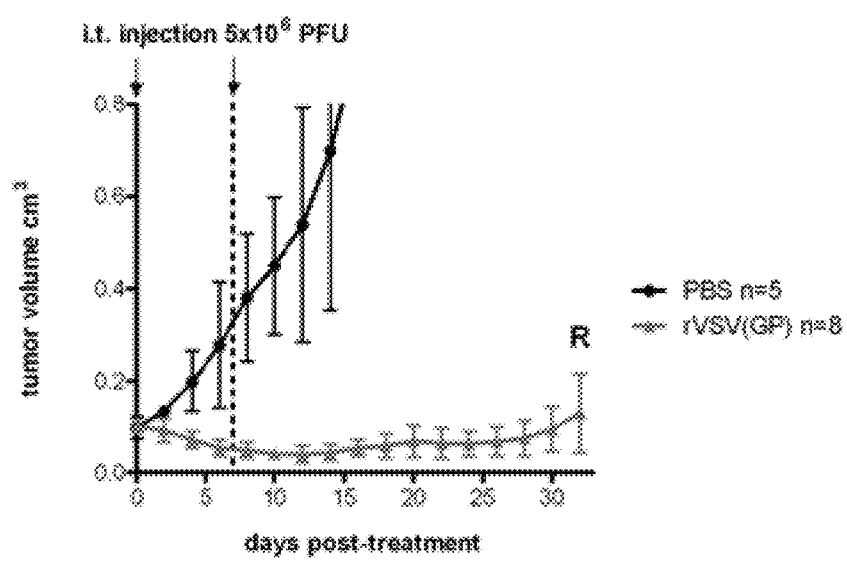
Figure 8D:
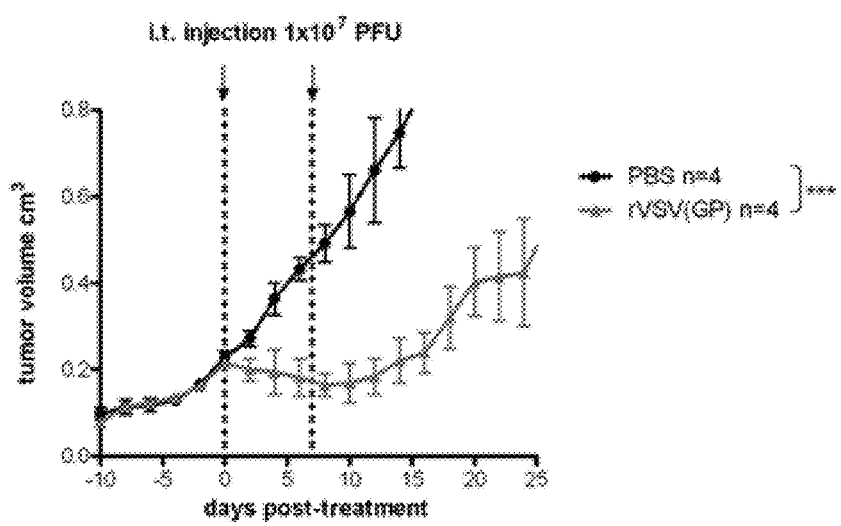

Corresponding to FIGS. 8C and 8D, subcutaneous A2780 tumors were treated i.t. with two doses of $5 \times 10^6$ PFU rVSV(GP) and tumor growth was monitored until relapse (R) was observed, as illustrated in FIG. 8C. Relapsing tumors were treated at a size of 0.2 cm³ with two doses of $1 \times 10^7$ PFU rVSV(GP) or PBS, as illustrated in FIG. 8D. Animals were sacrificed at a tumor size of 0.8 cm³. i.t. intratumoral; ***, $P<0.001$.

The results in FIGS. 8A-8D demonstrate that VSV-LCMV-GP treatment has antitumor activity in ovarian cancer xenografts and that relapsing tumors are still susceptible to oncolysis after treatment with VSV-LCMV-GP.

Example 9: Treatment of Prostate Tumors

Figure 9A:
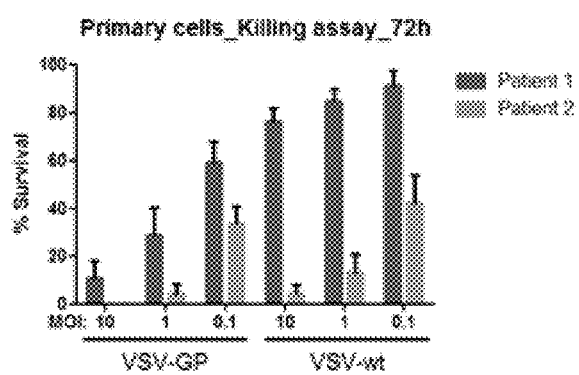
FIGS. 9A-9C are exemplary illustrations of some methods of use of VSV (LCMV-GP) to treat of prostate tumors, according to one embodiment.
Figure 9B:
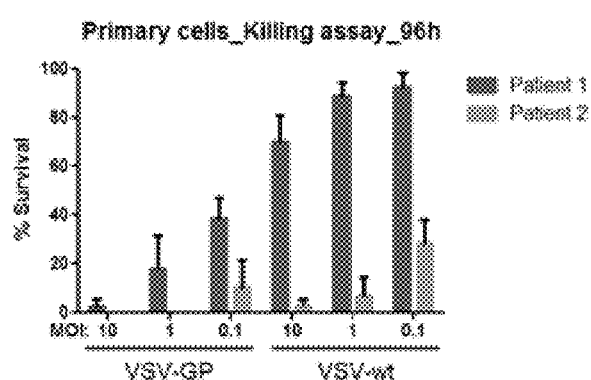

Exemplary experiments were conducted to test the anti-tumor efficacy of VSV-LCMV-GP in a prostate cancer model. Cultures of primary prostate cancers (PCa) cells were isolated directly from patient material and experiments were performed to test whether VSV-LCMV-GP can kill primary cultures of PCa cells. Cells were plated in 96-well plates and infected with either VSV wt or VSV-GP at MOI (i.e., multiplicity of infection) 10, 1 or 0.1. Cell survival was analyzed using a WST-1 reagent assay 72 and 96 hours after infection. Percent of survival was calculated using the mock infected sample as a reference representing 100% survival. Data are means and SD of 12 replicates. As illustrated in FIGS. 9A and 9B, primary PCa cells from two patients were efficiently killed by treatment with VSV-LCMV-GP, as compared to VSV-wt controls, after both 72 hours (FIG. 9A) and 96 hours (FIG. 9B).

Additionally, the anti-tumor efficacy of VSV-LCMV-GP was tested in a mouse xenograft model. Human PCa cells (e.g., Du145 at $2 \times 10^6$) were injected subcutaneously into the flanks of Rag2$^{-/-}$ γ$^{-/-}$-immunodeficient mice, generating two tumors per mouse. When the tumor reached 0.07 cm³, six animals (about 12 tumors) were treated with two local intratumoral injections of $10^7$ PFU VSV-LCMV-GP per tumor. Four control animals received injections of PBS only. Seven days after the first treatment, animals received a second dose. Animals were followed up for 58 days. VSV-wt was not used, as the maximal tolerated intratumoral dose was found to be only 10 infectious viruses (PFU) in immunodeficient mice. At higher doses, which would be required to achieve a therapeutic effect, all immunodeficient animals died of encephalitis. These data, illustrated in FIG. 9C, demonstrate that VSV-LCMV-GP treatment was able to eliminate the prostate tumors in mice, without relapse, up to 58 days post treatment.

Figure 9C:
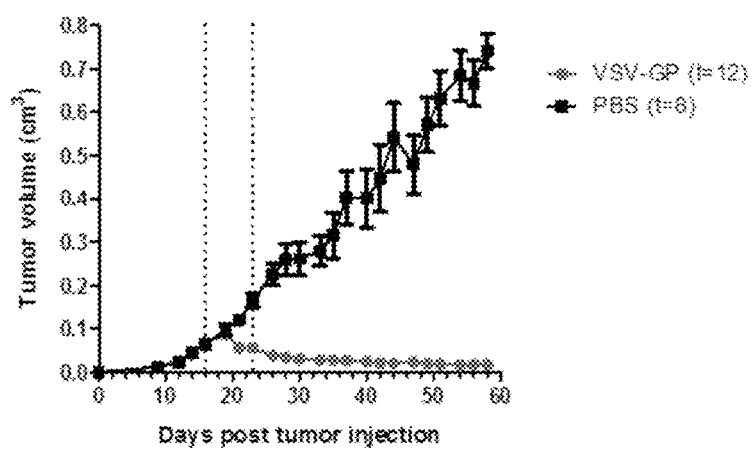

FIGS. 9A-9C illustrate primary cultures of PCa cells produced high titers of VSV-LCMV-GP and were efficiently killed by VSV-LCMV-GP treatment. Additionally, VSV-LCMV-GP treatment cured mice of prostate cancer in a mouse xenograft model.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method for treating a subject having one or more solid tumors, the method comprising:
   administering to the subject, a pharmaceutical composition comprising a therapeutically effective amount of a tumor-specific replication competent Vesicular stomatitis virus (VSV) pseudotyped vector having a gene encoding a glycoprotein (GP) of lymphocytic choriomeningitis virus (LCMV) (VSV-LCMV-GP pseudotype vector) and the vector either lacks a functional gene coding for envelope protein G of VSV or the envelope protein G is replaced;

wherein infection of cells with the replication competent VSV-LCMV-GP pseudotyped vector causes LCMV-GP to be encoded in the genome of progeny viral particle and subsequently expressed on the surface of the progeny viral particle and wherein tropism of the progeny viral particles is independent of an additional tumor-targeting element or transgene in the VSV-LCMV-GP pseudotype vector and wherein the progeny viral particle exhibits tumor-specific replication competence;

wherein the one or more solid tumors is selected from the group consisting of a reproductive tumor, an ovarian tumor, a testicular tumor, an endocrine tumor, a gastrointestinal tumor, a liver tumor, a kidney tumor, a colon tumor, a colorectal tumor, a bladder tumor, a prostate tumor, a skin tumor, melanoma, a respiratory tumor, a lung tumor, a breast tumor and a bone tumor; and wherein the pharmaceutical composition comprises a pharmaceutically acceptable carrier or excipient and wherein the pharmaceutical composition treats the solid tumor in the subject.

2. The method of claim 1, wherein the pharmaceutical composition comprising the VSV-LCMV-GP pseudotyped vector is administered to the subject using at least one intravenous administration.

3. The method of claim 1, wherein the pharmaceutical composition comprising the VSV-LCMV-GP pseudotyped vector is administered to the subject using at least one intratumoral administration.

4. The method of claim 1, wherein the pharmaceutical composition comprising the VSV-LCMV-GP pseudotyped vector is administered to the subject at a dose ranging from $1 \times 10^5$ to $1 \times 10^{15}$ plaque forming units (PFU).

5. The method of claim 1, wherein the administering to the subject a pharmaceutical composition further comprises contacting directly the one or more solid tumors with a therapeutically effective amount of the VSV-LCMV-GP pseudotyped vector.

6. The method of claim 1, wherein the pharmaceutical composition comprises one or more cells capable of producing the therapeutically effective amount of the VSV-LCMV-GP pseudotyped vector.

7. The method of claim 6, wherein the one or more cells comprises a multipotent adult progenitor cell (MAPC), a neuronal stem cell (NSC), a mesenchymal stem cell (MSC), a bone marrow derived tumor infiltrating cell (BM-TIC cells), or a combination thereof.

8. The method of claim 1, wherein the VSV-LCMV-GP pseudotyped vector further comprises one or more transgenes.

9. The method of claim 8, wherein the one or more transgenes encodes at least one of a suicide protein, an immunostimulatory protein, a marker protein, or a combination thereof.

10. The method of claim 8, wherein the one or more transgenes encodes at least one of thymidine kinase of the herpes simplex virus (HSV-TK), cytosine deaminase, FKBP-FAS, or FKBP-caspase-9.

11. The method of claim 8, wherein the one or more transgenes encodes at least one of interleukin-2 (IL-2), IL-4, IL-12, neutralizing anti-TGFbeta, or Flt3L or combination thereof.

12. The method of claim 1, wherein the pharmaceutical composition further comprises an anti-tumor agent.

13. The method of claim 12, wherein the anti-tumor agent comprises a chemotherapy drug, a platinum complex, a mitotic inhibitor, an alkylating agent, an anti-metabolite, an anti-tumor antibiotic, a DNA topoisomerase inhibitor, or a combination thereof.

14. A method of treating melanoma in a subject, the method comprising:
administering to the subject a pharmaceutical composition comprising a therapeutically effective amount of a replication competent Vesicular stomatitis virus (VSV) pseudotyped vector having a gene encoding the envelope glycoprotein (GP of the lymphocytic choriomeningitis virus (LCMV) as a replacement for endogenous glycoprotein G of the VSV pseudotyped vector,
wherein the pharmaceutical composition comprises a pharmaceutically acceptable carrier or excipient, and
wherein the pharmaceutical composition treats the melanoma in the subject.

15. The method of claim 14, wherein the pharmaceutical composition comprising the VSV-LCMV-GP pseudotyped vector is administered to the subject at a dose ranging between about $1 \times 10^5$ to about $1 \times 10^{15}$ PFU.

16. A method of treating ovarian cancer in a subject, the method comprising:
administering to the subject a pharmaceutical composition comprising a therapeutically effective amount of a replication competent Vesicular stomatitis virus (VSV) pseudotyped vector having a gene encoding the envelope glycoprotein (GP) of the lymphocytic choriomeningitis virus (LCMV) as a replacement for endogenous glycoprotein G of the VSV pseudotyped vector,
wherein the pharmaceutical composition comprises a pharmaceutically acceptable carrier or excipient, and
wherein the pharmaceutical composition treats the ovarian cancer in the subject.

17. The method of claim 16, wherein the pharmaceutical composition comprising the VSV-LCMV-GP pseudotyped vector is administered to the subject at a dose ranging from $1 \times 10^3$ to $1 \times 10^{10}$ PFU.

18. The method of claim 16, wherein the pharmaceutical composition further comprises an anti-tumor agent.

19. A method of treating prostate cancer in a subject, the method comprising:
administering to the subject a pharmaceutical composition comprising a therapeutically effective amount of a replication competent Vesicular stomatitis virus (VSV) pseudotyped vector having a gene encoding the envelope glycoprotein (GP) of the lymphocytic choriomeningitis virus (LCMV) as a replacement for endogenous glycoprotein G of the VSV pseudotyped vector,
wherein the pharmaceutical composition comprises a pharmaceutically acceptable carrier or excipient, and
wherein the pharmaceutical composition treats the prostate cancer in the subject.

20. The method of claim 19, wherein the pharmaceutical composition comprising the VSV-LCMV-GP pseudotyped vector is administered to the subject at a dose ranging from $1 \times 10^3$ to $1 \times 10^{10}$ PFU.

21. The method of claim 1, wherein the glycoprotein GP of the VSV-LCMV-GP pseudotyped vector is unmutated.

22. A method for treating a subject having a glioblastoma, the method comprising:

administering to the subject, a pharmaceutical composition comprising a therapeutically effective amount of a tumor-specific replication competent Vesicular stomatitis virus (VSV) pseudotyped vector having a gene encoding a glycoprotein (GP) of lymphocytic choriomeningitis virus (LCMV) (VSV-LCMV-GP pseudotype vector) and the vector either lacks a functional gene coding for envelope protein G of VSV or the envelope protein G is replaced;

wherein infection of cells with the replication competent VSV-LCMV-GP pseudotyped vector causes LCMV-GP to be encoded in the genome of progeny viral particle and subsequently expressed on the surface of the progeny viral particle and wherein tropism of the progeny viral particles is independent of an additional tumor-targeting element or transgene in the VSV-LCMV-GP pseudotype vector and wherein the progeny viral particle exhibits tumor-specific replication competence;

wherein the pharmaceutical composition comprises a pharmaceutically acceptable carrier or excipient and wherein the pharmaceutical composition treats the glioblastoma in the subject.

23. The method of claim 1, wherein the one or more solid tumors is selected from the group consisting of an ovarian tumor, a colon tumor, a prostate tumor, a melanoma, or a lung tumor.

* * * * *